US009354166B2

(12) United States Patent (10) Patent No.: US 9,354,166 B2
Judkewitz et al. (45) Date of Patent: May 31, 2016

(54) TIME-REVERSAL OF VARIANCE-ENCODED LIGHT (TROVE)

(71) Applicant: California Institute of Technology, Pasadena, CA (US)

(72) Inventors: Benjamin Judkewitz, Los Angeles, CA (US); Ying Min Wang, Pasadena, CA (US); Roarke Horstmeyer, San Marino, CA (US); Changhuei Yang, Alhambra, CA (US)

(73) Assignee: California Institute of Technology, Pasadena, CA (US)

( * ) Notice: Subject to any disclaimer, the term of this patent is extended or adjusted under 35 U.S.C. 154(b) by 98 days.

(21) Appl. No.: 14/070,045

(22) Filed: Nov. 1, 2013

(65) Prior Publication Data

US 2014/0118739 A1 May 1, 2014

Related U.S. Application Data

(60) Provisional application No. 61/721,325, filed on Nov. 1, 2012.

(51) Int. Cl.

| G01N 21/49 | (2006.01) |
|---|---|
| G01N 29/24 | (2006.01) |
| G01N 21/17 | (2006.01) |
| G01N 21/47 | (2006.01) |
| G01N 21/64 | (2006.01) |
| G01N 21/51 | (2006.01) |

(52) U.S. Cl.
CPC ............ *G01N 21/49* (2013.01); *G01N 21/1702* (2013.01); *G01N 21/1717* (2013.01); *G01N 21/4795* (2013.01); *G01N 21/6456* (2013.01); *G01N 29/2418* (2013.01); *G01N 2021/1708* (2013.01); *G01N 2021/1727* (2013.01); *G01N 2021/516* (2013.01)

(58) Field of Classification Search
None
See application file for complete search history.

(56) References Cited

U.S. PATENT DOCUMENTS

| 8,450,674 B2 | 5/2013 | Yang et al. |
| 8,525,998 B2 | 9/2013 | Yaqoob et al. |
| 8,717,574 B2 | 5/2014 | Yang et al. |

(Continued)

OTHER PUBLICATIONS

Aulbach, J., et al., "Control of Light Transmission through Opaque Scattering Media in Space and Time", Physical Review Letters 106, 103901 (2011), pp. 103901-1-103901-4.

(Continued)

*Primary Examiner* — Gordon J Stock, Jr.
(74) *Attorney, Agent, or Firm* — Gates & Cooper LLP

(57) ABSTRACT

A method and apparatus for irradiating a scattering medium with increased resolution. The method includes transmitting EM radiation from an Electromagnetic (EM) radiation source to a target inside a scattering medium, wherein the target encodes the EM radiation with a variance structure to form encoded EM radiation; measuring, in a detector, transmitted EM radiation comprising at least a portion of the encoded EM radiation transmitted through and exiting the scattering medium; decoding the transmitted EM radiation, comprising EM fields, in a computer, comprising selecting one or more of the EM fields having the variance structure; and irradiating the scattering medium with time reversed EM radiation from a spatial light modulator (SLM), the time reversed EM radiation generated from time reversing the EM fields having the variance structure, thereby forming a focus of the time reversed EM radiation in the scattering medium with the increased resolution.

25 Claims, 11 Drawing Sheets

(56) References Cited

U.S. PATENT DOCUMENTS

| | | | |
|---|---|---|---|
| 2009/0009834 A1 | 1/2009 | Yaqoob et al. | |
| 2011/0001980 A1 | 1/2011 | Yaqoob et al. | |
| 2011/0108707 A1 | 5/2011 | Cui et al. | |
| 2011/0122416 A1 | 5/2011 | Yang et al. | |
| 2011/0309267 A1 | 12/2011 | Cui et al. | |
| 2012/0307250 A1* | 12/2012 | Wang et al. | 356/450 |
| 2013/0342665 A1 | 12/2013 | Wang et al. | |
| 2014/0009808 A1* | 1/2014 | Wang et al. | 359/10 |

OTHER PUBLICATIONS

Cizmar, T., et al., "Exploiting multimode waveguides for pure fibre-based imaging", Nature Communications 3:1027, pp. 1-9, Aug. 28, 2012.

Conkey, D. B., et al., High-speed scattering medium characterization with application to focusing light through turbid media:, Optics Express, vol. 20, No. 2, pp. 1733-1740, Jan. 16, 2012.

Freund, I., "Looking Through Walls and Around Corners", Physica A 168, pp. 49-65, (1990).

Hsieh, C.-L., et al., "Digital phase conjugation of second harmonic radiation emitted by nanoparticles in turbid media", Optics Express, vol. 18, No. 12, pp. 12283-12290, Jun. 7, 2010.

Judkewitz, B., et al., "Speckle-scale focusing in the diffusive regime with time-reversal of variance-encoded light (TROVE)", Nature Photonics, vol. 7 (4), pp. 300-305, Apr. 2013.

Katz, O., et al., "Focusing and compression of ultrashort pulses through scattering media", Nature Photonics, vol. 5, pp. 372-377, Jun. 2011.

Katz, O., et al., "Looking around corners and through thin turbid layers in real time with scattered incoherent light", Nature Photonics, vol. 6, pp. 549-553, Aug. 2012.

Lai, P., et al., "Reflection-mode time-reversed ultrasonically encoded optical focusing into turbid media", Journal of Biomedical Optics, vol. 16(8), pp. 080505-1-080505-3, Aug. 2011.

Lerosey, G., et al., "Focusing Beyond the Diffraction Limit with Far-Field Time Reversal", Science, vol. 315, pp. 1120-1122, Feb. 23, 2007.

Liu, H., et al., "Time-reversed ultrasonically encoded optical focusing into tissue-mimicking media with thickness up to 70 mean free paths", Journal of Biomedical Optics, vol. 16(8), pp. 086009-1-086009-6, Aug. 2011.

Mosk, A. P., et al., "Controlling waves in space and time for imaging and focusing in complex media", Nature Photonics, vol. 6, pp. 283-292, May 2012.

Popoff, S., et al., "Image transmission through an opaque material", Nature Communications 1, 81, Sep. 21, 2010.

Popoff, S. M., et al., "Measuring the Transmission Matrix in Optics: An Approach to the Study and Control of Light Propagation in Disordered Media", Physical Review Letters 104, pp. 100601-1-100601-4, Mar. 12, 2010.

Redding, B., et al., "Speckle-free laser imaging using random laser illumination", Nature Photonics, vol. 6, pp. 355-359, Jun. 2012.

Si, K., et al., "Fluorescence imaging beyond the ballistic regime by ultrasound-pulse-guided digital phase conjugation", Nature Photonics, vol. 6, pp. 657-661, Oct. 2012.

Van Albada, M. P., et al., "Observation of Long-Range Intensity Correlation in the Transport of Coherent Light through a Random Medium", Physical Review Letters, vol. 64, No. 23, pp. 2787-2790, Jun. 4, 1990.

Van Putten, E. G., et al., "Scattering Lens Resolves Sub-100 nm Structures with Visible Light", Physical Review Letters 106, pp. 193905-1-193905-4, May 13, 2011.

Vellekoop, I. M., et al., "Focusing coherent light through opaque strongly scattering media", Optics Letters, vol. 32, No. 16, 2309-2311, Aug. 15, 2007.

Vellekoop, I. M., et al., "Exploiting disorder for perfect focusing", Nature Photonics 4, pp. 320-322, (2010).

Vellekoop, I. M., et al., "Digital optical phase conjugation of fluorescence in turbid tissue", Applied Physics Letters 101, pp. 081108-1-081108-4, 2012.

Wang, Y. M., et al., "Deep-tissue focal fluorescence imaging with digitally time-reversed ultrasound-encoded light", Nature Communications 3, (2012).

Xu, X., et al., "Time-reversed ultrasonically encoded optical focusing into scattering media", Nature Photonics, vol. 5, pp. 154-157, Mar. 2011.

Yamaguchi, I., et al., "Phase-shifting digital holography", Optics Letters, vol. 22, No. 16, pp. 1268-1270, Aug. 15, 1997.

Yaqoob, Z., et al., "Optical phase conjugation for turbidity suppression in biological samples", Nature Photonics, vol. 2, pp. 110-115, Feb. 2008.

Nature Photonics, Supplementary Information DOI: 10.1038/NPHOTON.2013.31, 2013, pp. 1-9, Macmillan Publishers Limited.

* cited by examiner

TIME-REVERSAL OF VARIANCE-ENCODED LIGHT (TROVE)

CROSS REFERENCE TO RELATED APPLICATIONS

This application claims the benefit under 35 U.S.C. Section 119(e) of the following commonly-assigned application:

U.S. Provisional Patent Application Ser. No. 61/721,325, filed on Nov. 1, 2012, by Benjamin Judkewitz, Ying Min Wang, Roarke Horstmeyer, and Changhuei Yang, entitled "TIME-REVERSAL OF VARIANCE ENCODED LIGHT", which application is incorporated by reference herein.

This application is related to the following commonly-assigned patent applications, which applications are incorporated by reference herein:

U.S. Utility patent application Ser. No. 13/851,901, filed on Mar. 27, 2013, by Ying Min Wang, Benjamin Judkewitz, Charles A. DiMarzio, and Changhuei Yang, entitled "DEEP TISSUE FLUORESCENCE IMAGING USING DIGITALLY TIME-REVERSED ULTRASOUND-ENCODED LIGHT", which application claims the benefit under 35 U.S.C. Section 119(e) of U.S. Provisional Patent Application Ser. No. 61/616,347, filed on Mar. 27, 2012, by Ying Min Wang, Benjamin Judkewitz, Charles A. DiMarzio, and Changhuei Yang, entitled "DEEP TISSUE FLUORESCENCE IMAGING USING DIGITALLY TIME-REVERSED ULTRASOUND-ENCODED LIGHT";

U.S. Utility patent application Ser. No. 12/886,320, filed on Sep. 20, 2010, by Zahid Yaqoob, Emily McDowell and Changhuei Yang, entitled "OPTICAL PHASE PROCESSING IN A SCATTERING MEDIUM", which application is a divisional of U.S. Utility patent application Ser. No. 11/868,394, filed on Oct. 5, 2007, by Zahid Yaqoob, Emily McDowell and Changhuei Yang, entitled "TURBIDITY ELIMINATION USING OPTICAL PHASE CONJUGATION AND ITS APPLICATIONS", which application claims priority under 35 U.S.C. §119(e) to commonly-assigned U.S. Provisional Patent Application Ser. No. 60/850,356, filed on Oct. 6, 2006, by Zahid Yaqoob, Emily McDowell and Changhuei Yang, entitled "TURBIDITY ELIMINATION USING OPTICAL PHASE CONJUGATION AND ITS APPLICATIONS";

U.S. patent application Ser. No. 12/943,857, filed on Nov. 10, 2010, by Changhuei Yang and Meng Cui, entitled "TURBIDITY SUPPRESSION BY OPTICAL PHASE CONJUGATION USING A SPATIAL LIGHT MODULATOR", which application claims the benefit under 35 U.S.C. §119(e) of the following commonly-assigned U.S. provisional patent applications, which are incorporated by reference herein:

a. Provisional Application Ser. No. 61/259,975, filed on Nov. 10, 2009, by Changhuei Yang and Meng Cui, entitled "APPROACHES FOR BUILDING COMPACT FLUORESCENCE MICROSCOPES";

b. Provisional Application Ser. No. 61/260,316, filed on Nov. 11, 2009, by Changhuei Yang and Meng Cui, entitled "APPLICATIONS OF TURBIDITY SUPPRESSION BY OPTICAL PHASE CONJUGATION");

c. Provisional Patent Application Ser. No. 61/376,202, filed on Aug. 23, 2010, by Meng Cui and Changhuei Yang, entitled "OPTICAL PHASE CONJUGATION 4PI MICROSCOPE"; and d. Provisional Application Ser. No. 61/355,328, filed on Jun. 16, 2010 by Meng Cui, Ying Min Wang and Changhuei Yang, entitled "ACOUSTIC ASSISTED PHASE CONJUGATE OPTICAL TOMOGRAPHY";

U.S. Utility application Ser. No. 12/943,841, filed on Nov. 10, 2010, by Meng Cui, Ying Min Wang, Changhuei Yang and Charles DiMarzio, entitled "ACOUSTIC ASSISTED PHASE CONJUGATE OPTICAL TOMOGRAPHY", which application claims priority under 35 U.S.C. §119(e) to commonly-assigned U.S. Provisional Application Ser. No. 61/355,328, filed on Jun. 16, 2010, by Meng Cui, Ying Min Wang, and Changhuei Yang, entitled "ACOUSTIC ASSISTED PHASE CONJUGATE OPTICAL TOMOGRAPHY"; U.S. Provisional Application Ser. No. 61/259,975, filed on Nov. 10, 2009, by Changhuei Yang and Meng Cui, entitled "APPROACHES FOR BUILDING COMPACT FLUORESCENCE MICROSCOPES"; U.S. Provisional Application Ser. No. 61/260,316, filed on Nov. 11, 2009, by Changhuei Yang and Meng Cui, entitled "APPLICATIONS OF TURBIDITY SUPPRESSION BY OPTICAL PHASE CONJUGATION"; and U.S. Provisional Patent Application Ser. No. 61/376,202, filed on Aug. 23, 2010, by Meng Cui and Changhuei Yang, entitled "OPTICAL PHASE CONJUGATION 4PI MICROSCOPE"; and U.S. Utility application Ser. No. 13/157,194, filed on Jun. 9, 2011, by Meng Cui, Ying Min Wang, and Changhuei Yang, entitled "ITERATIVE TIME-REVERSAL ENHANCED TRANSMISSION SOLVING APPROACH", which application claims the benefit under 35 U.S.C. §119(e) of Provisional Application Ser. No. 61/355,326, filed on Jun. 16, 2010, by Meng Cui, Ying Min Wang, and Changhuei Yang, entitled "ITERATIVE TIME-REVERSAL ENHANCED TRANSMISSION SOLVING APPROACH".

STATEMENT REGARDING FEDERALLY SPONSORED RESEARCH AND DEVELOPMENT

The invention was made with government support under OD007307 awarded by the National Institutes of Health. The government has certain rights in the invention.

BACKGROUND OF THE INVENTION

1. Field of the Invention

This invention relates to a method and apparatus for transmitting light in a scattering medium.

2. Description of the Related Art (Note: This application references a number of different publications as indicated throughout the specification by one or more reference numbers in brackets [x]. A list of these different publications ordered according to these reference numbers can be found below in the section entitled "References." Each of these publications is incorporated by reference herein.)

Scattering of light by inhomogeneous media poses a fundamental challenge to numerous applications in astronomy, biomedical imaging and colloidal optics. For a long time, scattered light has been viewed as a source of noise. Many advanced imaging approaches have been developed to filter it out, relying solely on the ballistic light component. However, this strategy is futile in strong scatterers, such as optical diffusers, paint or thick layers of biological tissue, which do not transmit a ballistic component. Focusing beyond the ballistic regime has therefore long been considered impossible.

Recent developments in the field of wavefront shaping have changed this view [1], demonstrating that scattered light can be utilized for optical focusing beyond the ballistic regime. As light travels across a strong scatterer, the wavefront leaving the sample is seemingly randomized. But, in fact, there is a linear mapping between the optical modes in the input wavefront and the optical modes in the output wavefront, which can be fully described by a scattering transmission matrix. These linear, deterministic and time-symmetric properties of scattering [2] have been harnessed for focusing and image transfer across complex samples by iterative wavefront optimization [3-8], time reversal [9,10], or directly measuring and inverting the transmission matrix [11-13].

Despite these significant advances in our understanding of wavefront control across scatterers, the methods outlined above require direct access to both sides of the scatterer (i.e. the input plane and the target plane). These approaches are therefore not directly applicable when the goal is to focus between scatterers or deep inside a scatterer. In such cases, wavefront optimization requires the assistance of beacons or so-called "guide-stars" in the target plane. Guide-stars have successfully been implemented using second-harmonic [14] or fluorescent [15] particles, but optical focusing inside scattering samples is limited to the vicinity of these stationary particles. An alternative approach, termed time reversal of ultrasound-encoded light (TRUE) [16-20], shows much promise for non-invasive imaging by taking advantage of virtual acousto-optic beacons. In this approach, an ultrasound focus frequency-shifts the scattered optical wavefront within a scattering sample, thus creating a source of frequency-shifted light. Scattered, frequency-shifted light emanating from this source is recorded outside the tissue and time-reversed by optical phase-conjugation to converge back onto the location of the ultrasound focus. Despite its ability to focus inside scattering samples at unprecedented depths, the resolution of TRUE imaging is fundamentally limited by the size of the ultrasound beacon, which is at least an order of magnitude larger (tens of micrometers at best) than the optical speckle size (micrometer-scale).

Here, the present invention proposes a way to break this resolution barrier imposed by the size of the beacon by time-reversal of variance-encoded light (TROVE). TROVE takes advantage of the spatially unique variance imposed by the acoustic field to encode the spatial location of individual optical speckles within the ultrasound focus. Upon optical time reversal of computationally decoded modes, one or more embodiments achieve focusing at the scale of single optical speckles with diffuse light.

SUMMARY OF THE INVENTION

Focusing of light in the diffusive regime inside scatterers has long been considered impossible. Recently, this limitation has been overcome with time reversal of ultrasound-encoded light (TRUE), but the resolution of this approach is fundamentally limited by the large number of optical modes within the ultrasound focus. Here, one or more embodiments of the present invention introduce a new approach, time reversal of variance-encoded light (TROVE), which demixes these spatial modes by variance-encoding to break the resolution barrier imposed by the ultrasound. By encoding individual spatial modes inside the scattering sample with unique variances, we effectively uncouple the system resolution from the size of the ultrasound focus. This enables us to demonstrate optical focusing and imaging with diffuse light at unprecedented, speckle-scale lateral resolution of ~5 μm. For example, one or more embodiments of the invention achieves speckle-scale focusing in the diffusive regime with TROVE.

For example, one or more embodiments of the invention disclose a method of irradiating a scattering medium with increased resolution, comprising: transmitting EM radiation from an Electromagnetic (EM) radiation source to a target inside a scattering medium, wherein the target encodes the EM radiation with a variance structure to form encoded EM radiation; measuring, in a detector, transmitted EM radiation comprising at least a portion of the encoded EM radiation transmitted through and exiting the scattering medium; decoding the transmitted EM radiation, comprising EM fields, in a computer, comprising selecting one or more of the EM fields having the variance structure; and irradiating the scattering medium with time reversed EM radiation from a spatial light modulator (SLM), the time reversed EM radiation generated from time reversing the EM fields having the variance structure, thereby forming a focus of the time reversed EM radiation in the scattering medium with the increased resolution.

The detector and SLM can be in a Digital Optical Phase Conjugation (DOPC) device and the scattering medium can include at least a portion that does not transmit a ballistic component of the EM radiation or wherein the scattering medium scatters the EM radiation in a diffusive regime.

The method can further comprise forming the EM radiation comprising a plurality of EM fields; transmitting signals from a signal generator to form the target comprising a plurality of spatially shifted and spatially overlapping signals, wherein each of the EM fields is encoded by each of the spatially shifted and spatially overlapping signals, to form the encoded EM radiation comprising a plurality of encoded fields and the transmitted EM radiation comprising a plurality of transmitted encoded fields; forming a plurality of matrices each representing a plurality of the transmitted encoded fields, wherein the transmitted encoded fields encoded by each of the spatially shifted and overlapping signals are represented in a different matrix; calculating a sum of the matrices and one or more differences of one or more pairs of the matrices; the decoding comprising finding a field vector v having higher variance for the sum and a smaller variance for the differences; and finding the complex conjugate of the field vector v; wherein the time reversed EM radiation comprises time reversed fields generated from the complex conjugate.

The decoding can further comprise calculating one or more variances or characteristics of variances of the transmitted EM radiation. For example, the decoding can comprise maximizing the Rayleigh Quotient of the matrices or solving an eigenvector equation comprising the Rayleigh Quotient and the vector is a principal eigenvector of the Rayleigh Quotient.

The method can further comprise forming four of the spatially shifted and overlapping signals and four of the matrices $C_1$, $C_2$, $C_3$, and $C_4$, wherein $$v = C_{1+2}(C_{1-2}C_{1-2}^*)^{-0.5} \cdot \text{eig}[(C_{1-2}C_{1-2}^*)^{-0.5} \cdot (C_{1+2}C_{1+2}^*)(C_{1-2}C_{1-2}^*)^{-0.5}].$$

The vector can represent a mode of zero variance in the differences of the matrices.

The method can further comprise randomizing the EM radiation to form the plurality of random EM fields.

The signals can be ultrasound foci that encode the EM fields to form the encoded EM fields comprising frequency shifted EM fields.

The method can further comprise shaping the ultrasound foci to produce the variance structure.

Each of the EM fields can produce different realizations r of the frequency-shifted EM fields, each realization r can be represented as a row of the matrices, and each row can comprise one of the encoded fields measured for one of the realizations.

The method can comprise measuring the frequency-shifted EM fields via digital phase-shifting holography.

The method can further comprise digitally scanning the time-reversed focus by weighing the fields in the matrices with prefactors that virtually and spatially move the intersection point of the signals.

The method can further comprise detecting, on a detector, output radiation based on an interaction between the time reversed EM radiation and the scattering medium, to produce a detected signal; and subtracting a background from the detected signal, in a computer, to obtain an output that at least approximates an interaction between a complete time reversed field, of all of the modulated EM radiation, and the target.

One or more embodiments further disclose an apparatus for irradiating a target in a scattering medium and a computer readable storage medium encoded with computer program instructions which when accessed by a computer cause the computer to load the program instructions to a memory therein creating a special purpose data structure causing the computer to operate as a specially programmed computer, executing a method of decoding transmitted EM radiation.

BRIEF DESCRIPTION OF THE DRAWINGS

Referring now to the drawings in which like reference numbers represent corresponding parts throughout:

FIG. 3a is a schematic of an experimental setup comprising a thin sheet of quantum dots between two strong diffusers, according to one or more embodiments of the invention.

FIG. 3b shows diffuse illumination observed without wavefront manipulation (flat phase display on the SLM).

FIG. 3c shows time reversal of ultrasound encoded (TRUE) light results in an optical focus the width of the ultrasound focus.

FIG. 3d shows that with the time reversal of variance encoded (TROVE) light technique, an optical focus the size of an optical speckle is achieved.

FIG. 3e shows the profile of the TRUE focus width.

FIG. 3f shows the profile of the TROVE focus width, wherein the number in brackets indicates the calculated resolution after deconvolving the profile with the resolution of the camera imaging the dotted square in FIG. 3a.

DETAILED DESCRIPTION OF THE INVENTION

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Technical Description

1. Principles

To better understand the resolution limitation of TRUE imaging and how we can overcome this limitation by variance encoding, we can conceptually divide any scattering medium into two sections: one, through which the input light passes before reaching the ultrasound focus, and a second, through which the ultrasound-shifted light passes on the way out of the medium. We can make this division without loss of generality for different illumination and recording geometries.

Figure 1:
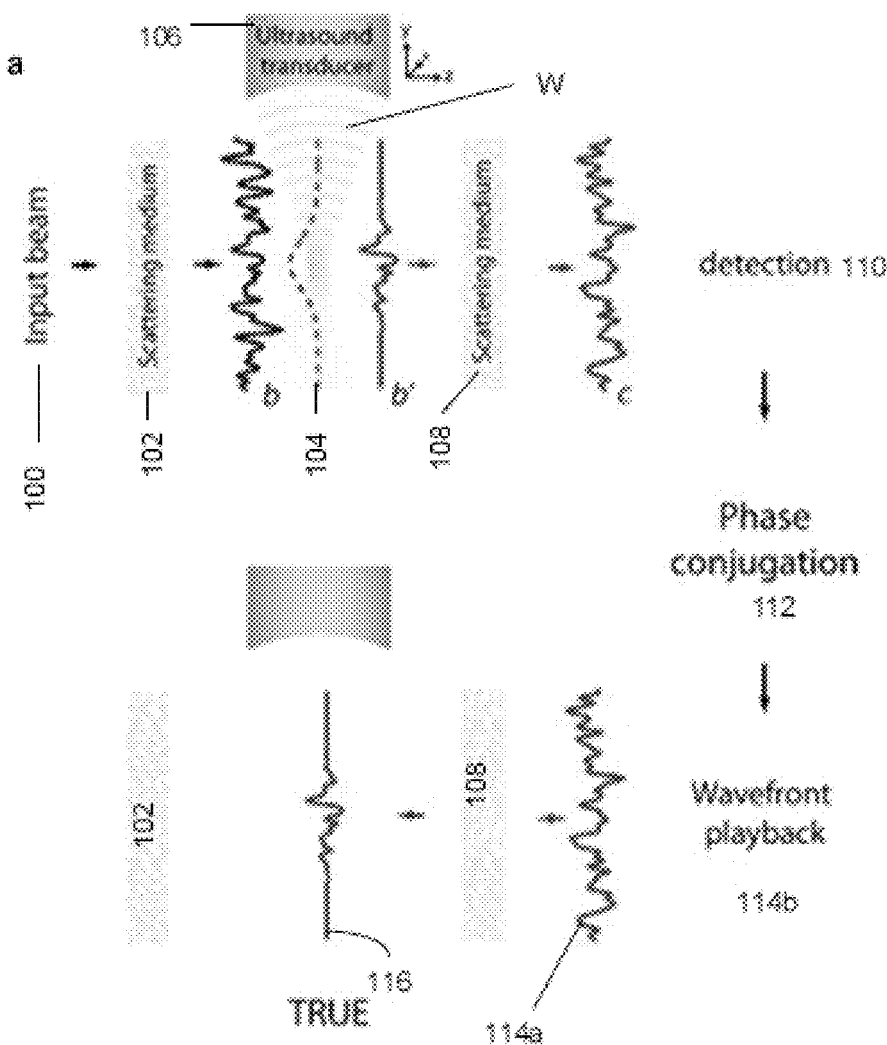
FIG. 1a is a schematic of the TRUE process.
FIG. 1b is a schematic of the scattering process and the setup, according to one or more embodiments of the invention, wherein an input wavefront illuminates the sample and is randomized as it reaches the ultrasound focal plane (represented as a 1D vector b), a fraction of the randomized wavefront passing the Gaussian shaped ultrasound focus (g) gets frequency-shifted by the acousto-optic effect (b') before propagating through the second tissue section (represented by the scattering matrix $T_{BC}$), the frequency-shifted wavefront leaving the tissue (c) is then selectively detected using digital phase-shifting holography, and as the input wavefront reaching the sample is randomized by rotating a diffuser disk, all realizations of the wavefronts can be inserted into the rows of one data matrix for each plane.
FIG. 1c illustrates exemplary shifted ultrasound foci $g_{1,2}$, wavefronts $b'_{1,2}$, and data sets $B'_{1,2}$ (displaying the absolute of the complex valued matrices), wherein, due to the complex normal statistics of speckle, the expected variance along the columns of $B'_{1,2}$ is $|g_{1,2}|^2$.
FIG. 1d illustrates sum (left) and difference (middle and right) data sets calculated from the two data sets shown in FIG. 1b, wherein it is noted that the expected variance along columns of $B'_{1-2}$ and $B'_{1+2}$ will follow $|g_1-g_2|^2$ and $|g_1+g_2|^2$, respectively, and on the right, difference of differentially weighted datasets, with shifted null-point of variance, are shown.
FIG. 1e illustrates a simulation of regular time reversal (TRUE focusing), resulting in a speckled optical focus the size of the ultrasound focus.
FIG. 1f illustrates a simulation of Time Reversal of Variance Encoded light (TROVE), resulting in a focus the size of an individual speckle which can be computationally shifted, wherein the plots show normalized intensity.
Figure 1:
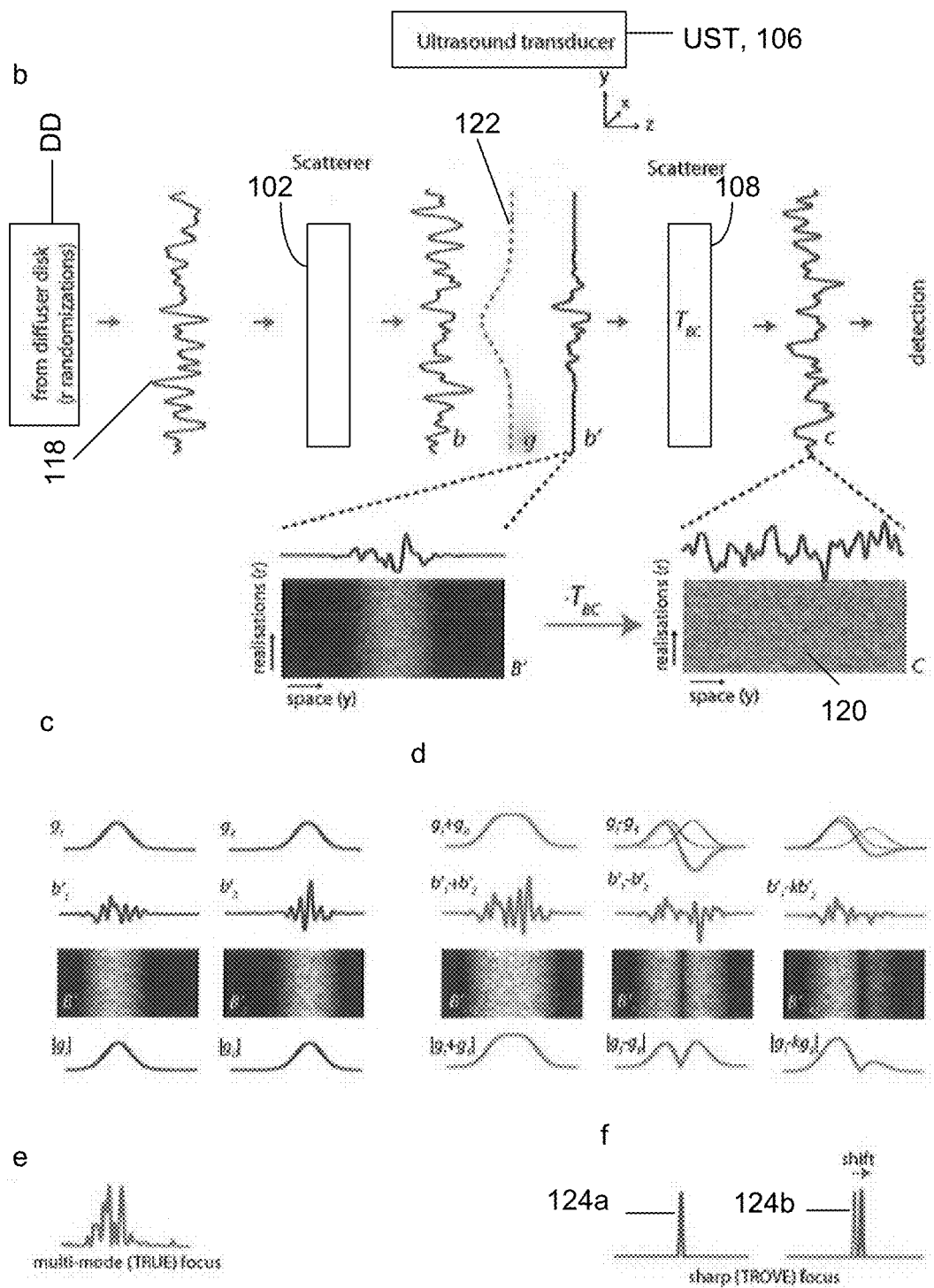

FIG. 1a illustrates the process of TRUE focusing, summarized by the following steps: First, an input wavefront 100 is randomized as it passes through the first scatterer or scattering medium 102. This results in a speckled wavefront b at the ultrasound focus 104 (of ultrasound W from an ultrasound transducer 106 translatable in x, y, and z directions), where b is a vector representing optical field values as a function of position. Part of this wavefront is frequency-shifted via the acousto-optic effect, resulting in a frequency-shifted optical field $b'=b \cdot G$ (where G denotes a diagonal matrix whose diagonal elements g describe the Gaussian-shaped ultrasound focus 104). Because the ultrasound focus is much larger than the optical wavelength, this field contains many optical modes—typically hundreds to thousands of optical speckles for a 30-40 µm wide ultrasound focus. Since we will eventually only measure and phase conjugate the frequency-shifted light, we need only consider the frequency-shifted components. Thus, b' can be thought of as a spatially confined, multimode source originating from the location of the ultrasound focus.

Next, b' propagates through the second section of the scattering medium 108 (mathematically described by the scattering matrix $T_{BC}$) before leaving the tissue as the output field $c=b' \cdot T_{BC}$. In other words, c can be described as a linear superposition of many optical transmission modes, or rows in $T_{BC}$, and the weights of this superposition are given by b'. This output field c is detected/measured 110 and subsequently time-reversed (phase conjugated 112). The time reversed wavefront 114a is played back 114b through the second section of the scatterer 108, resulting in a wavefront 116 that is an approximation to the conjugate of the field b' at the ultrasound focal plane (the recovery of the multi-modal focus at the location of the ultrasound plus background, as discussed in [3,19]). Thus, the limited resolution of TRUE is a result of the fact that all optical modes passing through the ultrasound focus are collectively detected and time-reversed.

In contrast to previous methods for focusing across scatterers [3-7,9-12] we do not have experimental access to b' because it is hidden within the sample. All we know about this wavefront is that that it consists of a mixture of many modes that spatially span over a Gaussian-shaped envelope, g, imposed by the ultrasound focus at a controllable location. To achieve micrometer-scale optical focusing, we would instead have to isolate a single mode corresponding to an individual row in $T_{BC}$. One or more embodiments of the present invention achieve this and overcome the problem of the low resolution of the ultrasound focus forcing us to record mixtures of many optical modes at the output plane.

FIGS. 1b-1d and 1f illustrate variance encoding of optical transmission modes, according to one or more embodiments of the invention.

The TROVE approach, illustrated in FIG. 1b, addresses this challenge by uniquely encoding the spatial location of the frequency-shifted optical speckles with a variance structure imposed by spatially shifted ultrasound foci. Here, we explain the important conceptual and experimental modifications to the conventional TRUE approach that enable TROVE. First, although we cannot measure or predict the speckle field b' without access to the ultrasound plane, we know that its envelope follows the shape of the ultrasound focus. Thus, over many possible realizations of b', the expected variance at each spatial location in the ultrasound plane will follow the square of the envelope. To implement random realizations of b', we add a rotating diffuser disk to the beam path leading to the sample. As the diffuser is rotated, each new diffuser position will result in a different realization of the input wavefront 118 (multiple randomizations from the diffuser disk DD) and thus different frequency-shifted wavefronts b' and c, at the ultrasound plane and the output plane, respectively. We can represent each realization r of b, b' and c as rows of the matrices B, B' and C respectively (FIG. 1b). The field 120 recorded outside the sample at each diffuser position or for each realization r (each row in C) will be a different linear combination of transmission modes (rows in $T_{BC}$) originating from individual optical modes within the ultrasound focus 122.

While the weights of this linear combination (given by b') are not known, we know that their variance, over the different random realizations, will follow the square of the ultrasound focus (g). This effectively encodes the spatial location of an optical mode within the ultrasound focus by its variance.

Since the Gaussian-shaped ultrasound focus is symmetric, more than one location in the ultrasound plane (more than one column in b') will experience the same level of variance. To resolve this ambiguity, we move the ultrasound focus 122 between two positions (1 and 2), resulting in slightly shifted foci $g_1$ and $g_2$, whose flanks overlap, as shown in FIG. 1c. It is important to note that the data for both foci is recorded for the same diffuser position, such that $B'_1=B \cdot G_1$ and $C_1=B'_1 \cdot T_{BC}$ for the first ultrasound focus location and $B'_2=B \cdot G_2$ and $C_2=B'_2 \cdot T_{BC}$ for the second. By taking the sum and the difference of $B'_1$ and $B'_2$, we get $B'_{1+2}$ and $B'_{1-2}$ (FIG. 1d). As illustrated in FIG. 1d, the amplitude of $B'_{1-2}$ across realizations is zero at the intersection of $g_1$ and $g_2$, because the underlying speckle patterns B for both data sets $B_1$ and $B_2$ are the same. As a result, the variance of $B'_{1-2}$ is zero along the column of this intersection. The spatial mode $b'_0$ at this intersection thereby becomes uniquely encoded as a mode of zero variance in the difference of the data sets ($B'_{1-2}$) and of high variance in the sum ($B'_{1+2}$). Since the variance structure of optical modes is preserved as they are transmitted through scatterers (see Supplementary Information [24], e.g., under the heading Derivation of a computationally efficient decoding algorithm, pages 4-8), we can also find this mode in the data set recorded at the output plane by searching for a vector v, along which the variance of $C_{1-2}$ is minimal and the variance of $C_{1+2}$ is high. Mathematically, we define the vector v as the one that maximizes the ratio between these two variances (this ratio is also known as the Rayleigh Quotient). A detailed description of our variance decoding procedure to find v can be found in the Supplementary Information [24] under the heading Derivation of a computationally efficient decoding algorithm, pages 4-8. The resultant vector v is equivalent to the field which would result from the transmission of a single optical mode ($b'_0$) at the location of the intersection of $g_1$ and $g_2$ through the scatterer represented by $T_{BC}$ (i.e. $v=b'_0 \cdot T_{BC}$). By using a digital spatial light modulator (SLM) to display the complex conjugate of v and letting it propagate back through the scatterer, we expect to obtain a high-resolution phase conjugate focus at the location of the intersection of the shifted foci, $g_1$ and $g_2$.

Although we assumed (and measured) that the ultrasound foci are Gaussian-shaped, it is worth noting that the validity and performance of the TROVE method does not hinge upon the exact shape of the ultrasound focus, as long as shifted foci intersect such that difference of the data sets ($B'_{1-2}$) presents a sharp null point.

2. Simulations

As a first confirmation of our ability to encode and decode individual spatial transmission modes, we implemented the TROVE framework in a numerical simulation (see FIG. 1b). As shown in FIG. 1a, we generated complex normal random matrices B and $T_{BC}$ and chose two overlapping 1-D Gaussian functions $g_1$ and $g_2$, representing the shifted ultrasound foci that convert B into $B'_1$ and $B'_2$, respectively (see section 7 for details). We then calculated the matrices $C_1$ and $C_2$ that would have been measured outside the scatterer in a real experiment. With the decoding strategy outlined above, using only $C_1$–$C_2$, we calculated the vector v that maximized the ratio of variances along $C_{1+2}$ and $C_{1-2}$. When this vector was time-reversed (multiplied by $T_{BC}$* in the simulation), we were able to achieve a tight speckle-sized focus 124a at the intersection of the two functions $g_1$ and $g_2$ (see FIG. 1f). Comparatively, when we simulated the TRUE framework by time-reversing one row of either the $C_1$ or the $C_2$ matrix, we found that the resultant field consisted of a multimode focus, the size of the much larger Gaussian-shaped ultrasound ($g_1$ or $g_2$), as shown in FIG. 1e.

A straightforward way to shift the TROVE focus, or access other optical modes at different positions, would be to move the location of the ultrasound foci. This would entail repeating the entire TROVE measurement to assemble a new set of matrices, $C_1$ and $C_2$. However, the TROVE strategy allows access to multiple optical modes within the ultrasound focus without the need for further acquisition of data matrices. We note that the location of the TROVE focus is entirely determined by the point at which the shifted ultrasound foci intersect (see above). Thus, by numerically weighing the matrices $C_1$ and $C_2$ with respect to each other during post-processing, we can virtually move the point of intersection (and thus the TROVE focus) to any location along the common axis of the shifted ultrasound foci (dotted shifted focus 124b in FIG. 1f).

3. Characterization of Frequency-Shifted Field

FIG. 2a-j illustrate characterization of frequency-shifted wavefronts at the ultrasound plane, according to one or more embodiments of the invention.

Figure 2:
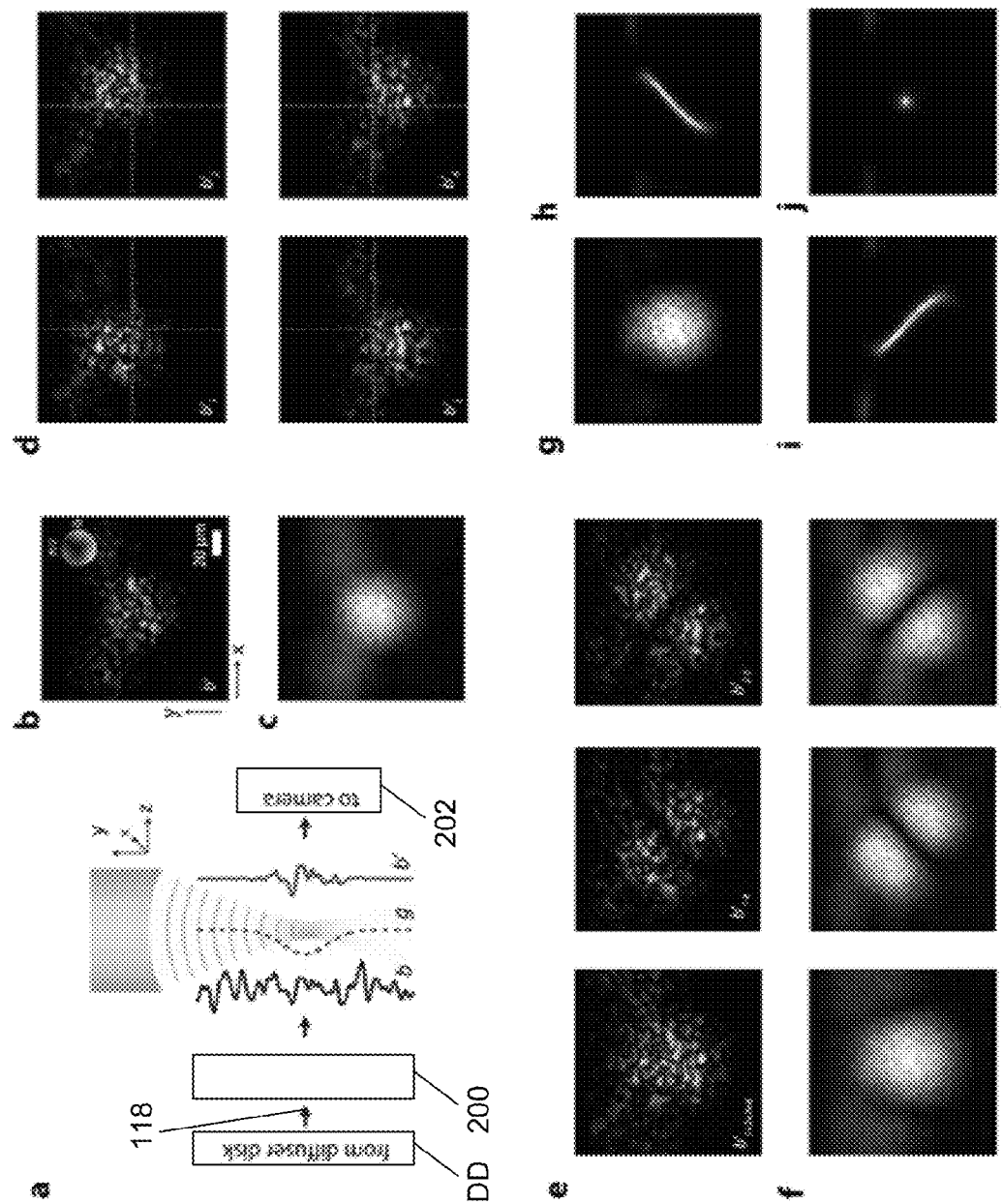
FIG. 2a is a schematic of a recording setup according to one or more embodiments, in which the second scatterer is absent to allow optical access to the field b' from the right.
FIG. 2b shows a typical frequency shifted speckle field at the plane of the ultrasound focus.
FIG. 2c shows the average amplitude of the frequency shifted optical speckle field over 1000 realizations.
FIG. 2d illustrates the complex ultrasound frequency-shifted field at the plane of the ultrasound focus for four shifted locations of the ultrasound, wherein it can be noticed that the underlying speckle pattern is the same, but the ultrasound-modulated envelopes are shifted, color represents phase, and luminance represents normalized amplitude.
FIG. 2e illustrates complex fields of the sum and the pair-wise difference of the fields in FIG. 2a, respectively.
FIG. 2f illustrates average amplitude of the fields shown in FIG. 2e over 1000 realizations.
FIG. 2g illustrates variance across realizations of $b_{1+2+3+4}$ (variance along $B_{1+2+3+4}$).
FIG. 2h illustrates variance along $B_{1+2+3+4}$ divided by variance along $B_{1-4}$.
FIG. 2i illustrates variance along $B_{1+2+3+4}$ divided by variance along $B_{2-3}$.
FIG. 2j illustrates variance along $B_{1+2+3+4}$ divided by the sum of variances along $B_{1-4}$ and $B_{2-3}$.

The previous sections demonstrated the working principles of the TROVE technique in a two dimensional conceptual framework with one-dimensional scanning. To confirm this approach experimentally and to extend its utility to two-dimensional scanning, we first sought to measure and characterize the frequency-shifted field B' at the ultrasound focus. We do so by constructing a sample 200 consisting of an agarose-filled glass cuvette with a strong diffuser on the side of the input light such that no detectable ballistic component reaches the ultrasound plane (FIG. 2a). In the absence of a second scatterer, we imaged the frequency-shifted wavefront at the ultrasound plane via digital phase-shifting holography (see Methods section). Also shown are ultrasound transducer and camera 202 for imaging the scattered light.

FIG. 2b shows a typical frequency shifted speckle field at the plane of the ultrasound focus. FIG. 2c shows the average amplitude of the frequency shifted optical speckle field over 1000 realizations.

To unambiguously encode and shift the TROVE focus in two dimensions, we slightly modified the strategy described in the previous section—instead of using two overlapping ultrasound foci, we used four overlapping ultrasound foci ($g_1$, $g_2$, $g_3$, $g_4$) arranged in a square grid. FIG. 2d shows the representative complex maps of the frequency-shifted fields $b'_{1,2,3,4}$. FIG. 2e shows the complex sum of the four shifted fields $b'_{1+2+3+4}$ and the pairwise difference between the diagonal fields ($b'_{1-4}$ and $b'_{2-3}$) respectively. By moving the diffuser and repeating the measurement for 1000 random presentations of the input wavefront, we obtained an average amplitude map of the frequency-shifted optical field. As shown in FIG. 2f, the average amplitude along the difference for each pair of the two diagonally arranged foci, $B'_{1-4}$ and $B'_{2-3}$, yielded a null zone, which was absent in the average intensity map of $B'_{1+2+3+4}$. This null zone in the average of speckle images is also apparent in their variance across realizations. As can be seen in FIG. 2j, the ratio between the variance along $B_{1+2+3+4}$, divided by the sum of variances along $B_{1-4}$ and $B_{2-3}$ had a peak at the intersection of the four Gaussians, uniquely defining that point. Drawing from the intuition established in our simulations, we can effectively shift this intersection in two dimensions by scaling the relative weights between $B'_1$ and $B'_4$, and between $B'_2$ and $B'_3$ and recalculating the above ratio.

While these results confirm that we indeed get a null point at the ultrasound plane, we need to keep in mind that our ultimate goal is to accomplish focusing through scattering media. Consequently, we would not have access to speckle data at the ultrasound plane. Instead of analyzing data matrices at the ultrasound plane, we would only be able to record and analyze the matrices at the output plane. However, thanks to the preservation of variance across scatterers, as discussed above, we can still find the desired mode by looking for a vector v along which the variance of the measured data $C'_1 - C'_4$ and $C'_2 - C'_3$ is minimal and the variance of the sum ($C_1 + C_2 + C_3 + C_4$) is maximal. The adapted mathematical expression for finding the vector v can be found in the methods section.

4. Direct Visualization of TROVE Focus

FIG. 3a-f illustrate visualization of speckle-scale optical focusing, according to one or more embodiments of the invention. To demonstrate that the TROVE approach can used to focus inside a scattering sample, we created a sample 300 consisting of a glass cuvette flanked on both sides by strong diffusers 302 that do not transmit a detectable ballistic component (see Methods and FIG. 3*a*). We filled the cuvette with agarose containing a thin quantum dot sheet, so the TROVE focus could be observed via fluorescence excitation. Also shown are the ultrasound transducer 304 translatable in x, y and z directions, input light 306, and light from the SLM 308.

Figure 3:
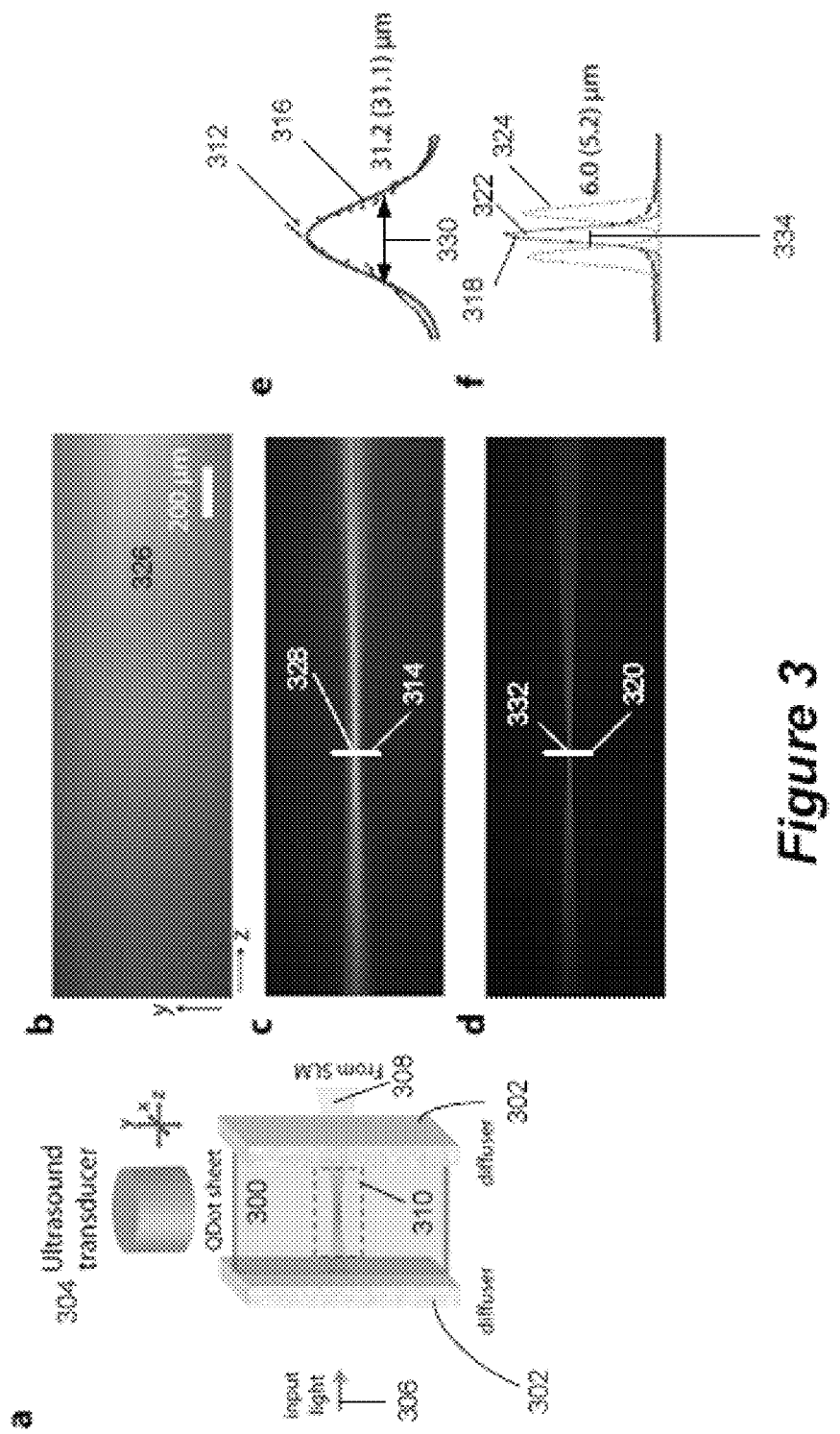

FIGS. 3*b-d* are fluorescence emission images of the area in y-z plane indicated by the dotted square 310 in FIG. 3*a*, wherein the scale bar is 200 µm.

FIG. 3*e* shows the profile of the TRUE focus width and FIG. 3*f* shows the profile of the TROVE focus width, wherein the black dots 312 are data points measured along the cross-section 314 in FIG. 3*c* (solid line 316 is the fit), the black dots 318 are data points measured along the cross-section 320 in FIG. 3*d* (solid line 322 is the fit), and the dotted lines 324 represent profiles of TROVE foci scanned in y (scan locations separated by 10 µm).

Without any wavefront manipulation, we observed that light 326 was highly diffused and failed to form a focus within the sample (FIG. 3*b*). Using the TRUE focusing approach and digitally phase conjugating an unprocessed phase map from a single realization, we observed a focus 328 with a full width half maximum (FWHM 330) of 31.2 µm, on the same order of magnitude as the size of the ultrasound focus (30 µm) (FIGS. 3*c* & *e*). When implementing the TROVE framework, we achieved a focus 332 having a size or FWHM 334 of 5.2 µm, which is close to the optical speckle size in our sample (5 µm FWHM) of the intensity autocorrelation) (FIGS. 3*d* & *f*). Thus, the TROVE method yielded a six-fold improvement over the TRUE focusing approach. A direct consequence of the reduction of optical modes in the TROVE focus, as compared to the TRUE focus, was an increase in the peak signal intensity of the time-reversed focus (as discussed in [19]). We observed in our experiments that the peak signal intensity with TROVE increased by a factor of 20, as compared to TRUE.

5. Imaging with the TROVE Focus

FIGS. 4*a-h* illustrate point spread function and image acquisition, according to one or more embodiments of the invention, wherein locations of data points are indicated by red dots 400, data is interpolated for display using bicubic interpolation, and the scale bar is 10 µm.

Figure 4:
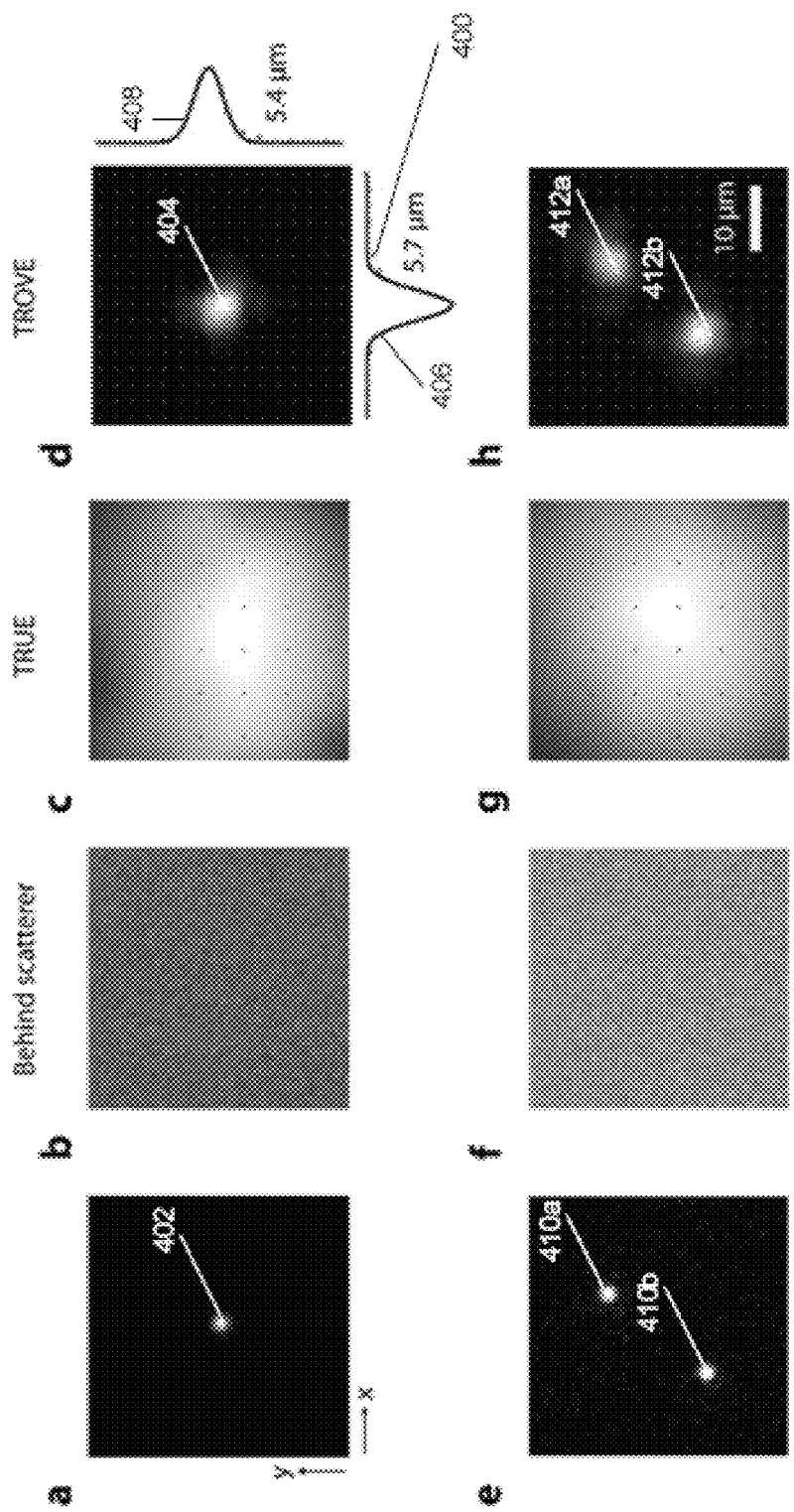
FIG. 4a shows an epifluorescence image of a single bead.
FIG. 4b shows an epifluorescence image of a single bead as seen through a diffuser.
FIG. 4c shows a fluorescence image of a single bead obtained by raster-scanning a TRUE focus.
FIG. 4d shows a fluorescence image of a single bead obtained using TROVE focusing and scanning technique and also shows the profiles of the fluorescent bead in the x and y directions.
FIG. 4e shows an epifluorescence image of two fluorescent beads before being placed between strong diffusers.
FIG. 4f shows an epifluorescence image of beads placed behind a diffuser.
FIG. 4g shows a fluorescence image of single bead obtained by raster-scanning a TRUE focus.
FIG. 4h shows the TROVE focusing and scanning technique resolves the two beads placed between the strong diffusers.

We demonstrate the TROVE focusing and two-dimensional scanning strategy established above by scanning the TROVE focus in two-dimensions over a 1 µm diameter fluorescent bead 402 (FIG. 4*a*) placed in a cuvette flanked by strong diffusers. We confirmed that, due to scattering, the bead could not be imaged via conventional epifluorescence (FIG. 4*b*). To acquire a TROVE image, we used a photomultiplier tube placed outside the sample to collect the backscattered fluorescence signal, excited by the scanned TROVE foci. From the TROVE image 404 acquired, we obtained the point spread functions 406, 408 having FWHM of 5.7 µm and 5.4 µm in the x and y direction, respectively (FIG. 4*d*). As compared to TRUE focusing [19] shown in FIG. 4*c*, we again find a resolution improvement of over six fold.

We further demonstrate this resolution improvement by scanning two 1 µm diameter fluorescent beads 410*a*, 410*b* placed 15 µm apart (FIG. 4*e*). Due to the limited resolution of the TRUE technique, the TRUE image does not resolve the individual beads (FIG. 4*g*). In comparison, the two beads 410*a-b* are well-resolved with TROVE imaging (see FIG. 4*h*, showing TROVE images 412*a* and 412*b* of beads 410*a*, 410*b*).

6. Discussion

In this work we presented a new method—time reversal of variance-encoded light (TROVE), to focus light at unprecedented, speckle-scale resolution in the diffusive regime. We demonstrated an optical setup that encoded frequency-shifted speckles originating from an ultrasound guide star with a unique variance structure, as well as a decoding algorithm that enabled the measurement and subsequent time reversal of individual optical transmission modes between highly diffusive scatterers. We characterized the lateral point spread function of an embodiment of the system to be 5.4 µm by 5.7 µm micrometers, a six fold improvement compared to previous methods [19, 20]. Beyond just resolution improvement, TROVE provides a means to computationally access different optical modes within the ultrasound focus, enabling control of optical wavefronts within a scattering sample at speckle-scale resolution. We demonstrated this ability to access different optical modes from a single dataset by two-dimensional scanning and imaging of fluorescent features.

In essence, the TROVE method uncouples the resolution of the system from the size of the ultrasound guide star. The resolution of the system is instead fundamentally determined by the size of the optical speckles at the ultrasound plane. Due to the low numerical aperture of illumination in our experiments, the size of the optical speckles was 5 µm (full width at half maximum, FWHM). The size of the speckles could be made smaller with different illumination configurations to yield higher resolution. However, this would require a corresponding increase in the number of wavefront measurements required, resulting in longer acquisition times.

This is an important trade-off because TROVE is based on optical time reversal, and is thus crucially reliant on the mechanical stability of the sample. Therefore, the duration of wavefront measurements and decoding computations should be shorter than the decorrelation time of the sample. In our demonstration, the time required for the measurement of a data set that enabled us to access a 30 µm by 30 µm field of view was 2 hours. Although current hardware speeds restrict the applicability of our method to mechanically stable samples, we anticipate that this requirement can be significantly relaxed with the advent of faster cameras, spatial light modulators [21] and wavefront scramblers such as random lasers [22].

With these improvements on the horizon, one or more embodiments of our method paves the way for micrometer-scale optical focusing, imaging, and image transfer inside a wide range of highly diffusive media.

7. Measurement and Simulation Methods a. Optical Setup

Figure 5:
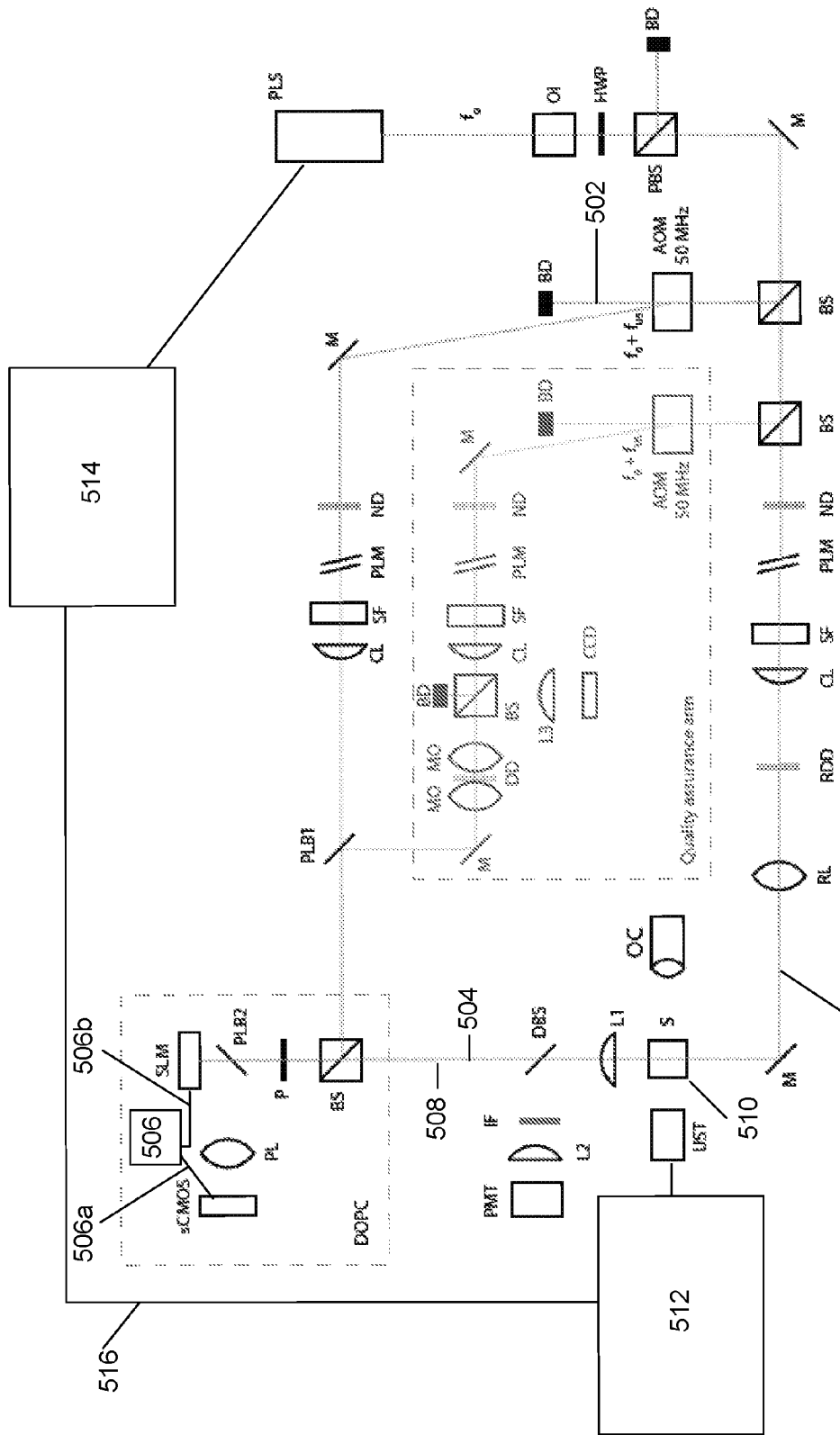
FIG. 5 is setup diagram used to acquire data according to one or more embodiments, wherein the abbreviations are Pulsed laser source (PLS), Optical Isolator (OI), Half-wave plate (HWP), Polarizing beamsplitter (PBS), Beam dump (BD), Mirror (M), 50/50 cube beamsplitter (BS), Acousto-optic modulator (AOM), Neutral density filter-wheel (ND), Path length matching arm (PLM), Single-mode fiber acting as spatial filter (SF), Collimating lens (CL), Sample (S), Ultrasound transducer (UST), 50 mm planoconvex lens (L1), Dichroic beamsplitter (DBS), Interference filter (IF), 25 mm planoconvex lens (L2), Photomultiplier tube (PMT), Polarizer (P), 90/10 plate beamsplitter (PLB1), Digital optical phase conjugation setup (DOPC), 50/50 plate beamsplitter (PLB2), Photography compound lens (PL), sCMOS camera (sCMOS), Spatial light modulator (SLM), 300 mm planoconvex lens (L3), Microscope objective (MO), Diffuser disk (DD), Diffuser Disk on Rotation mount (RDD), Relay lens system (RL) imaging the illuminated spot on the diffuser disk onto the sample (RL), Observing camera (OC).

All data shown was acquired using a custom built setup that was based on our previously described work on fluorescence TRUE imaging [19], as shown in FIG. 5. FIG. 5 illustrates a 2.7 W, 532 nm Q-switched laser PLS (Navigator, Spectra-Physics, USA) pulsed at 20 kHz with a pulse width of 7 ns and a coherence length of 7 mm was used as a light source. After passing an optical isolator OI and a fixed attenuator, it was split into a reference beam 500 and a sample beam 502 using a beam splitter BS. The sample beam was attenuated by a neutral density filter wheel ND, spatially filtered by a single mode optical fibre SF (Nufern 460HP, 20 cm length), collimated to a 0.8-mm waist beam using collimating lens CL, and directed onto an optical diffuser disk on a rotation mount RDD. The diffuse light exiting the disk was relayed to the surface of our sample S with an irradiance of <10 mW/mm$^2$.

Inside the sample S, a fraction of the light was frequency-shifted by an ultrasound transducer UST (element size: 6.35 mm, focal length: 6 mm; V3330, Olympus NDT, Olympus, USA) operated at 50 MHz. To achieve maximal resolution along the axis of ultrasound propagation, the transducer UST was driven with short pulses (50 MHz, 100 V peak-to-peak carrier oscillation with a Gaussian pulse envelope of 13 ns FWHM) triggered by the laser Q-switch signal at a fixed delay such that the ultrasound pulses coincided with the laser pulses at the same location, forming an ultrasound focus confined in three dimensions. To translate the ultrasound focus, the transducer UST was mounted on a three-axis computer-controlled micromanipulator (Sutter Instruments, USA). After passing through the sample, the scattered beam was recombined with the horizontally-polarized reference beam, which had also been frequency-shifted by an acousto-optic modulator AOM (AFM-502-A1, IntraAction, USA). After passing a horizontally-aligned polarizer and another beamsplitter BS, the combined beams reached the surface of a phase-only SLM (vis-PLUTO, Holoeye, Germany), carefully aligned (1:1 pixel-to-pixel match) to the image plane of a high dynamic range sCMOS camera (pco.edge, PCO AG, Germany).

b. Detection of Fluorescence Excitation by Time-Reversed Light

The time-reversed beam was obtained by reflecting the blank reference beam off the SLM displaying the computed phase conjugate map (see also [19]). To directly visualize the time-reversed focus, the fluorescence emission from the quantum dot sheet was imaged with a 4× magnification onto a digital camera OC fitted with a longpass filter (BLP02-561R, Semrock, USA) through the clear window between the diffusers (Stingray F145, AVT, USA).

This direct access was not utilized in subsequent experiments where fluorescent beads were imaged. For the TROVE imaging experiments, the emitted fluorescence that passed back through the scatterer was reflected off a dichroic mirror DBS (FF541-SDi01, Semrock, USA) and detected by a single-channel PMT (H7827-002, Hamamatsu, Japan) fitted with a bandpass filter IF (FF01-572/28, Semrock, USA). Because of the comparatively low contrast in the TRUE imaging experiments, a camera OC (Stingray F145, AVT, USA) was used to collect the fluorescence emitted through the clear window between the diffusers. It is important to note that the camera was not used to resolve the bead, but just as a single pixel detector to collect the fluorescence emitted. In TROVE and TRUE scanning experiments, we suppressed the fluorescence excited by the time reversal background with adaptive background subtraction (described in [19]).

c. Phase Recording

We recorded the frequency-shifted field at the SLM plane and the frequency-shifted field at the ultrasound plane with digital phase-shifting holography [23]. The carrier oscillation driving the Ultrasound (US) transducer UST was shifted by 0, $\pi/2$, $\pi$, and $3\pi/2$ phase delay relative to the oscillation driving the reference beam AOM and a frame was acquired for each phase delay. This 4-frame cycle was repeated 10 times and frames recorded at the same phase delay were averaged, resulting in four intensity maps that were used to reconstruct the complex field according to $E=(I_{\pi/2}-I_{3\pi/2})+i(I_0-I_\pi)$. To obtain phase maps for each of the four overlapping ultrasound focus locations required for TROVE, we translated the ultrasound focus laterally, using the micromanipulator (by 26 μm), and vertically, by adjusting the delay of the ultrasound pulses (by 20 nanoseconds (ns)) versus the laser pulses.

d. Calculation of Variance Encoded Modes

To find a vector for phase conjugation back to a single mode, we looked for a vector v with high variance along the sum $C_1+C_2$ (shorthand: $C_{1+2}$) and low variance along the difference $C_{1-2}$. We achieved this by maximizing the ratio of variances $Q_{ID}=v^*(C_{1+2}^*C_{1+2})v/(v^*(C_{1-2}^*C_{1-2})v)$. Since Q is a generalized Rayleigh Quotient, it can be maximized by $v=\text{eig}[(C_{1-2}^*C_{1-2})^{-1}\cdot(C_{1+2}^*C_{1+2})]$, where eig[ ] denotes a function returning the principal eigenvector. Because the size of C is 1000× 0.5M in our experiments (number of realizations by number of pixels on the detector), a direct calculation of this eigenvector would involve a 0.5M by 0.5M matrix and would be computationally impractical. In the Supplementary Information [24] (under the heading Derivation of a computationally efficient decoding algorithm, pages 4-8) we derive an alternative approximation of v that is computationally efficient because it only involves 1000×1000 matrices:

$$v=C_{1+2}(C_{1-2}C_{1-2}^*)^{-0.5}\cdot\text{eig}[(C_{1-2}C_{1-2}^*)^{-0.5}\cdot(C_{1+2}C_{1+2}^*)(C_{1-2}C_{1-2}^*)^{-0.5}].$$

To extend this framework to 2-D scanning, having collected four matrices $C_{1,2,3,4}$ (corresponding to the four foci arranged in a grid), we define the modified Rayleigh Quotient as $$Q_{2D}=v^*(C_{1+2+3+3}^*C_{1+2+3+4})v/(v^*(C_{1-3}^*C_{1-3}+C_{2-4}^*C_{2-4})v)$$

and maximize it as above. To digitally scan the time-reversed focus in space, we addressed different optical modes at the ultrasound focal plane by weighing the datasets $C_{1,2,3,4}$ with prefactors that virtually moved the intersection point of the Gaussian foci.

e. Simulation

Simulations of TRUE and TROVE focusing were implemented using custom routines written in MATLAB (The Mathworks). We followed the framework outlined in the Principles section and divided our simulations into three modules: First, we generated the complex random matrices $B_{1,2}$ (1000 repetitions by 200 pixels at ultrasound plane) and $T_{BC}$ (200 pixels at ultrasound plane by 1000 pixels at the detection plane; the size of $T_{BC}$ was chosen to be as large as the memory of our computer would permit). To simulate speckle autocorrelation, we convolved $B_{1,2}$ with a speckle autocorrelation function (a Gaussian of FWHM=5). We then chose Gaussian functions representing $g_{1,2}$ the ultrasound foci (FWHM=50, σ=21, shifted by 2σ) and calculated the matrices $C_{1,2}=B\cdot G_{1,2}\cdot T_{BC}$. Second, we performed the same analysis on $C_{1,2}$, which we also performed on experimentally measured data, to obtain the vector v maximizing the Rayleigh quotient (see above). Third, we simulated time-reversal of this vector by multiplying its complex conjugate by $T_{BC}^T$. Finally, the time-reversed focus was moved by computationally shifting the intersection point between the two Gaussian foci. This is achieved by changing the scalar k in the equation $C_{1-2}=C_1-kC_2$. The intersection between $g_1$ and $k\cdot g_2$ could be shifted predictably according to $k=2e^{x/\sigma}$ (where $g_1$ and $g_2$ are Gaussian functions whose means are separated by 2σ, and x is the shift of the intersection point).

f. Samples

The open-top quartz glass cuvette with four polished sides (Starna Cells, CA) was filled with 2% (wt/wt) agarose gel (Invitrogen, USA). The glass cuvette was flanked on two sides with highly diffusing films (3M) that did not transmit a detectable ballistic component (measured with a detection threshold of less than $10^{-8}$ of the transmitted power—see [19] for setup).

The quantum dot sheet used to directly visualize the time-reversed foci was made with Qtracker 655 (Non-targeted quantum dots, Invitrogen) diluted in agarose such that the final concentration of quantum dots was 0.4 μM.

The 1 μm diameter fluorescent beads (FluoSphere, Orange fluorescent) used for point spread function characterization and imaging demonstration were obtained from Invitrogen, USA.

8. Process Steps

Figure 6:
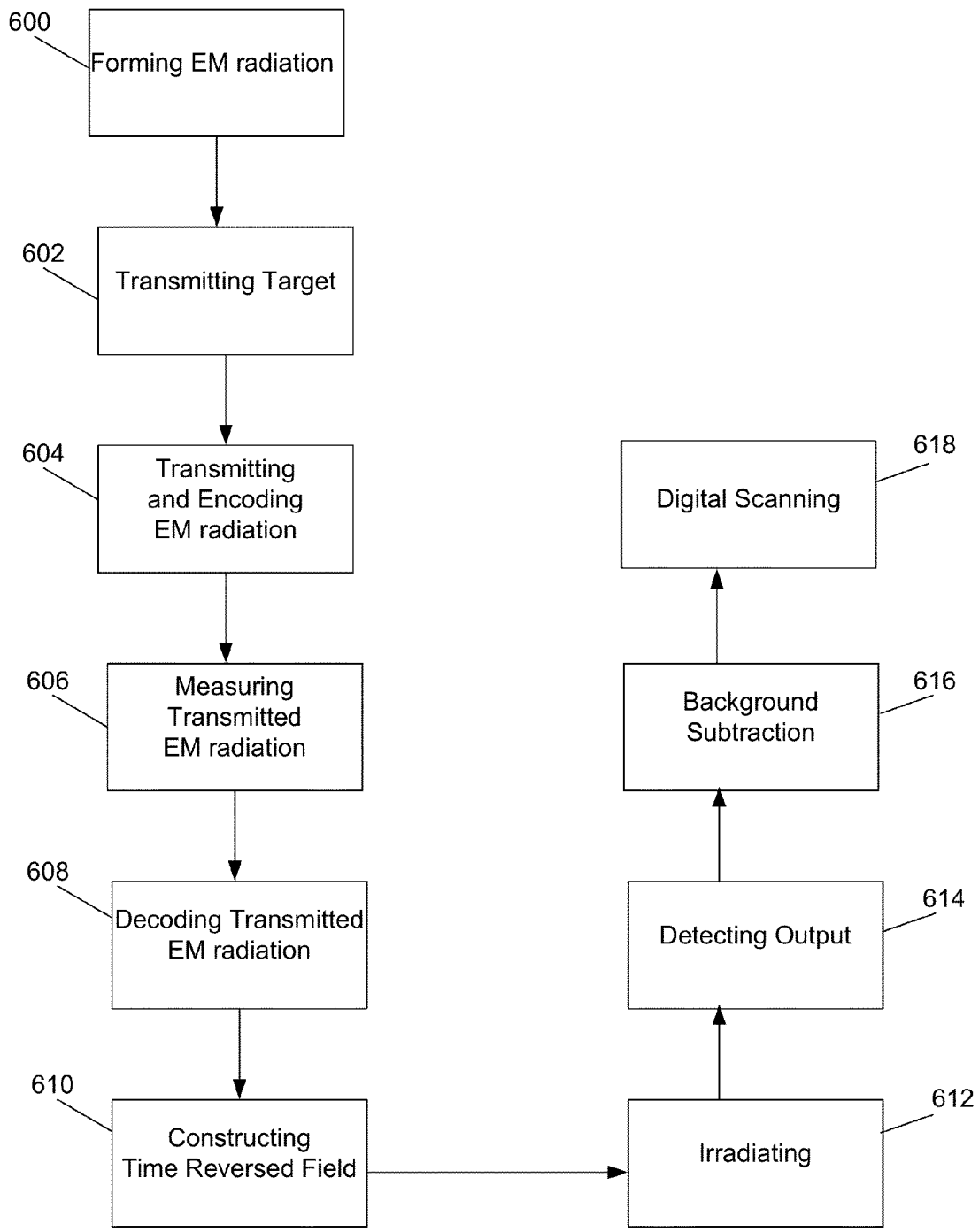
FIG. 6 is a flowchart illustrating a method according to one or more embodiments of the present invention.

FIG. 6 illustrates a method of irradiating a scattering medium with increased resolution, according to one or more embodiments. The method can comprise the following steps (steps can be added or omitted, as appropriate).

Block 600 represents forming the Electromagnetic (EM) radiation (e.g., light) comprising a plurality of EM fields. The forming can comprise randomizing the EM radiation, e.g., to form a plurality of random EM fields (e.g., at least 1000 different random EM fields).

Block 602 represents transmitting signals from a signal generator/source of signals (e.g., source of ultrasound) to form a target or guide star inside a scattering medium. The target can comprise a plurality of spatially shifted and spatially overlapping signals.

The signals can be ultrasound foci that encode the EM fields to form the encoded EM fields comprising frequency shifted EM fields. The step can further comprise shaping the ultrasound foci to produce the variance structure.

Block 604 represents transmitting the EM radiation from an EM radiation source to a target inside a scattering medium, thereby encoding/modulating the EM radiation at the target. The target can encode the EM radiation with a variance structure to form modulated/encoded EM radiation. Each of the EM fields can be encoded by each of the spatially shifted and spatially overlapping signals, to form the encoded EM radiation comprising a plurality of encoded fields and the transmitted EM radiation comprising a plurality of transmitted encoded fields.

The encoding can encode spatial transmission modes of the EM radiation at the target with a signal and a variance.

The scattering medium (e.g., animal, human, or plant tissue) can include at least a portion that does not transmit a ballistic component of the EM radiation or wherein the scattering medium scatters the EM radiation in a diffusive regime.

Block 606 represents measuring, in a detector system or detector, transmitted EM radiation comprising at least a portion of the encoded EM radiation (comprising encoded fields) transmitted through and exiting the scattering medium. The measuring can include measuring at least a portion of the encoded fields that have exited the scattering medium, as transmitted encoded fields. The measuring can comprise measuring the transmitted EM fields comprising frequency-shifted EM fields via digital phase-shifting holography (e.g., using the method illustrated in Blocks 610a-c of [26]).

Block 608 represents decoding the transmitted EM radiation, comprising EM fields, in a computer, comprising selecting one or more of the EM fields having the variance structure, e.g., using a decoding algorithm, e.g., as illustrated in FIG. 7. The step can comprise measuring or observing the variance structure in the encoded/transmitted EM radiation exiting the scattering medium.

The step can comprise decoding output spatial modes of the transmitted EM radiation having the variance structure.

The decoding can comprise calculating one or more variances or characteristics of variances of the transmitted EM radiation. The step can comprise searching/observing a sign/signature/effect/figure or merit of the variance structure in the transmitted EM radiation to decode the transmitted EM radiation.

Block 610 represents constructing EM fields. The step can comprise time reversing/optical phase conjugation of the EM fields having the variance structure. The step can comprise time reversing the output spatial modes having the variance structure.

Figure 7A:
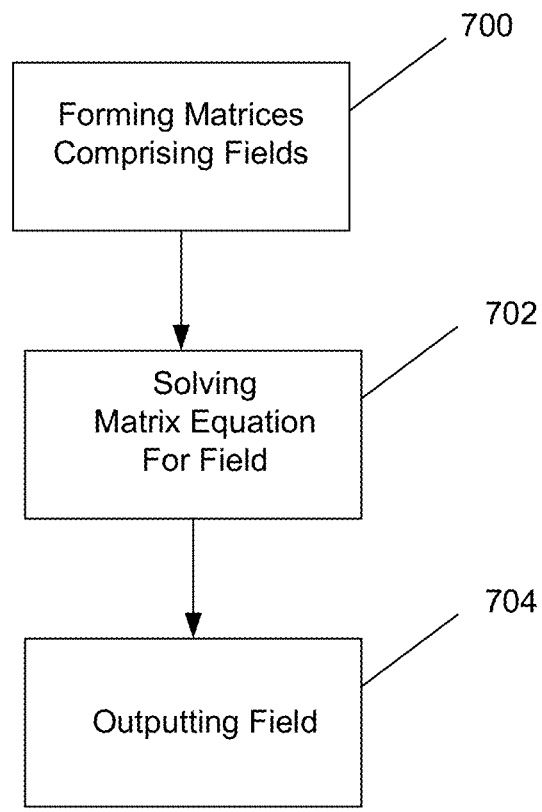
FIG. 7a is a flowchart illustrating a decoding algorithm according to one or more embodiments of the present invention.
Figure 7B:
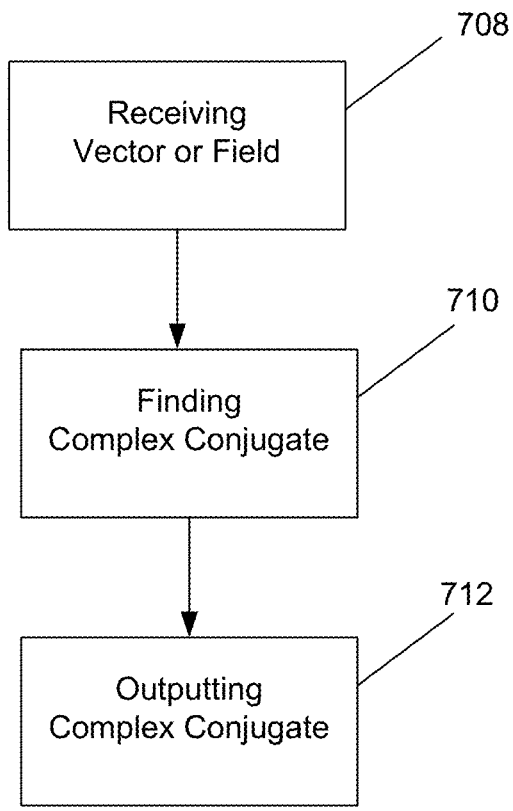
FIG. 7b is a flowchart illustrating a method of time reversing, according to one or more embodiments of the invention.

Block 612 represents irradiating the scattering medium with time reversed EM radiation (e.g., from a spatial light modulator and/or formed using the method of FIG. 7b) generated from time reversing the EM fields/output spatial modes having the variance structure, thereby forming a focus (defined by the target) of the time reversed EM radiation in the scattering medium with the increased resolution. The EM radiation can form speckle at the target and the variance structure can be such that a size of the focus is at most limited by the speckle. The variance structure can be such that a spatial extent of the focus is at most 10 micrometers.

Block 614 represents detecting, on a detector, output radiation based on an interaction between the time reversed EM radiation and the scattering medium/target (e.g., fluorescence), to produce a detected signal.

Block 616 represents subtracting a background from the detected signal, in a computer, to obtain an output that at least approximates an interaction between a complete time reversed field, of all of the modulated EM radiation, and the target (e.g., using the methods of [26].

Block 618 represents digitally scanning the time-reversed focus by weighing the fields in the matrices with prefactors that virtually and spatially move the intersection point of the signals.

FIG. 7a is a flowchart illustrating a decoding algorithm according to one or more embodiments of the invention, which can be implemented in one or more computers.

Block 700 represents forming a plurality of matrices or arrays each representing a plurality of the transmitted encoded fields measured and received 506a from the detector (e.g., sCMOS), wherein the transmitted encoded fields encoded by each of the spatially shifted and overlapping signals are represented in a different matrix. For example, there can be four matrices $C_1$, $C_2$, $C_3$, and $C_4$, for each of four spatially shifted and overlapping signals.

Each of the EM fields can produce different realizations r of the frequency-shifted EM fields, each realization r can be represented as a row of the matrices, and each row can comprise one of the encoded fields measured for one of the realizations.

Block 702 represents finding/searching for/calculating the one or more transmitted encoded fields (e.g., represented by one or more vectors v) in the matrices having the variance structure (see [24] at pages 4-8).

The step can comprise solving a matrix equation.

The step can comprise calculating a sum of the matrices and one or more differences of one or more pairs of the matrices and finding one or more vector fields v having higher variance for the sum of the matrices and a smaller variance for the differences of the matrices. The step can comprise finding a vector v representing a mode of zero variance in the differences.

The step can comprise finding a vector v which maximizes the Rayleigh Quotient Q of the matrices. The step can comprise solving an eigenvector equation comprising the Rayleigh Quotient and the vector v, wherein the vector v is a principal eigenvector of the Rayleigh Quotient.

The step can comprise solving an eigensystem equation comprising the matrices and an eigenvector v associated with the maximum eigenvalue of the general eigensystem. With four matrices $C_1$, $C_2$, $C_3$, and $C_4$, the eigensystem equation can be $$(C_{1+2}{}^*C_{1+2})v = (C_{1-2}{}^*C_{1-2})\lambda v \qquad (1)$$

wherein $$v = \mathrm{eig}[(C_{1-2}{}^*C_{1-2})^{-1} C_{1+2}{}^*C_{1+2}] \qquad (2)$$

where eig[ ] represents a principal eigenvector identification operator.

The eigensystem equation (2) can comprise m×r matrices, where n is the number of pixels of speckle data (pixels on the detector sCMOS) and r is the number of realizations. The eigensystem equation (2) can be computationally evaluated more quickly and with greater ease by applying approximations (see [24] at pages 4-8) such as those set forth below, which lead to finding a solution based on two r×r Gram matrices.

1. First, the complex random Gaussian transmission matrix $T_{BC}$ for the scattering medium can be assumed to satisfy $T_{BC}T_{BC}^*=I$ (appropriate for phase conjugation) where I is the identity matrix and the associated error in the approximation approaches zero as $T_{BC}$ increases in size and has more open channels (e.g., as in biological tissue). See also [27].
2. Second, it can be assumed that the matrix B is a complex random Gaussian leading to the approximation $B^*B \approx I$ and $BB^* \approx I$, wherein the approximation improves as m approaches r.
3. Third, refocusing to a small delta function like spot at position x, which is equivalent to determining one row of $T_{BC}$. This can be achieved by searching for a solution of the form $v=(d(x) T_{BC})^*$ where $d(x)$ is a row vector with 1 in row x and 0's elsewhere. Such solution is found by setting $G=G_{1+2}$ and searching for a mode x near the intersection of the summed Gaussian ultrasound signals, and leads to the approximation $BG_{1+2}T \approx BT$.

The equation can also be rewritten to involve an eigen decomposition of a Hermitian matrix.

The above approximations lead to a finding a vector for two dimensional (2D) scanning $v=C_{1+2+3+4}^{*-0.5} (C_{1-4}C_{1-4}^* + C_{2-3}C_{2-3}^*)^{-0.5} \cdot \text{eig}[(C_{1-4}C_{1-4}^* + C_{2-3}C_{2-3}^*)^{-0.5} \cdot (C_{1+2+3+4} C_{1+2+3+4}^*)(C_{1-4}C_{1-4}^* + C_{2-3}C_{2-3}^{*-0.5})]$.

In one dimension (1D), $v=C_{1+2}(C_{1-2}C_{1-2}^*)^{-0.5} \cdot \text{eig}[(C_{1-2}C_{1-2}^*)^{-0.5} \cdot (C_{1+2}C_{1+2}^*)(C_{1-2}C_{1-2}^*)^{-0.5}]$ (see section 7d above).

One or more embodiments select a scattering medium, number of realizations r, shape/envelope of the signal producing the variance structure (e.g., Gaussian), and a focus size (e.g., delta function) wherein one or more of the above approximations hold true.

Block 704 represents outputting the vector(s) v representing the decoded transmitted EM radiation.

FIG. 7b is a flowchart illustrating a method of forming time reversed EM radiation according to one or more embodiments of the invention, which can be implemented in one or more computers.

Block 708 represents receiving the field vector(s) v representing the decoded transmitted EM radiation.

Block 710 represents finding the complex conjugate of the vector field(s) v (e.g., using the method illustrated in Block 610d or Block 710 of [26]).

Block 712 represents outputting 506b the complex conjugate field(s), e.g., to a spatial light modulator SLM, wherein the time reversed EM radiation comprises time reversed fields generated from the complex conjugate.

One or more embodiments of the invention can be implemented using the apparatus illustrated in FIG. 5.

FIG. 5 illustrates an apparatus for irradiating a target in a scattering medium, comprising an ultrasound transducer UST providing a target inside a scattering medium; a coherent Electromagnetic (EM) radiation source, e.g., laser PLS, for transmitting EM radiation 500 to the target inside a scattering medium, wherein the target encodes the EM radiation 500 with a variance structure to form encoded/modulated EM radiation 504; and a digital optical phase conjugation device (DOPC) positioned to measure transmitted EM radiation comprising at least a portion of the encoded EM radiation transmitted through and exiting the scattering medium, the DOPC comprising a detector sCMOS to receive the transmitted EM radiation 504 comprising EM fields; a computer 506 configured to decode the transmitted EM radiation, wherein the computer 506 (e.g., in communication 506b, 506a with detector sCMOS and SLM) selects one or more of the EM fields having the variance structure; and a spatial light modulator (SLM) irradiating the scattering medium S with time reversed EM radiation 508 generated from time reversing the EM fields having the variance structure, thereby forming a focus of the time reversed EM radiation in the scattering medium S with the increased resolution.

The UST can transmit ultrasound waves that define the target inside the scattering medium; the EM radiation can comprise spatial modes wherein the target modulates variance of the spatial modes transmitted to the target with a variance structure, to form the modulated EM radiation. The DOPC can measure/find the output spatial modes of transmitted EM radiation comprising the modulated EM radiation that has exited the scattering medium having the variance structure, and construct a time reversed EM field comprising the output spatial modes having the variance structure. The SLM can irradiate the scattering medium with an EM field comprising time reversed fields of the output spatial modes having the variance structure, thereby forming a focus of the EM field defined by the target; and The apparatus can further comprise a translatable sample holder 510 supporting the scattering medium and/or moving the scattering medium, and one or more computers 512, 514 (e.g., in communication 516) controlling (e.g., timing/output of) the UST and PLS.

The computers 506, 512, 514 can include microprocessors or microcontrollers or chips. For example, the CMOS detector and SLM could be driven with an Arduino microcontroller, hooked up to a source of flash memory. Another example is a Raspberry Pi (with additional flash memory, for example).

9. Hardware Environment

Figure 8:
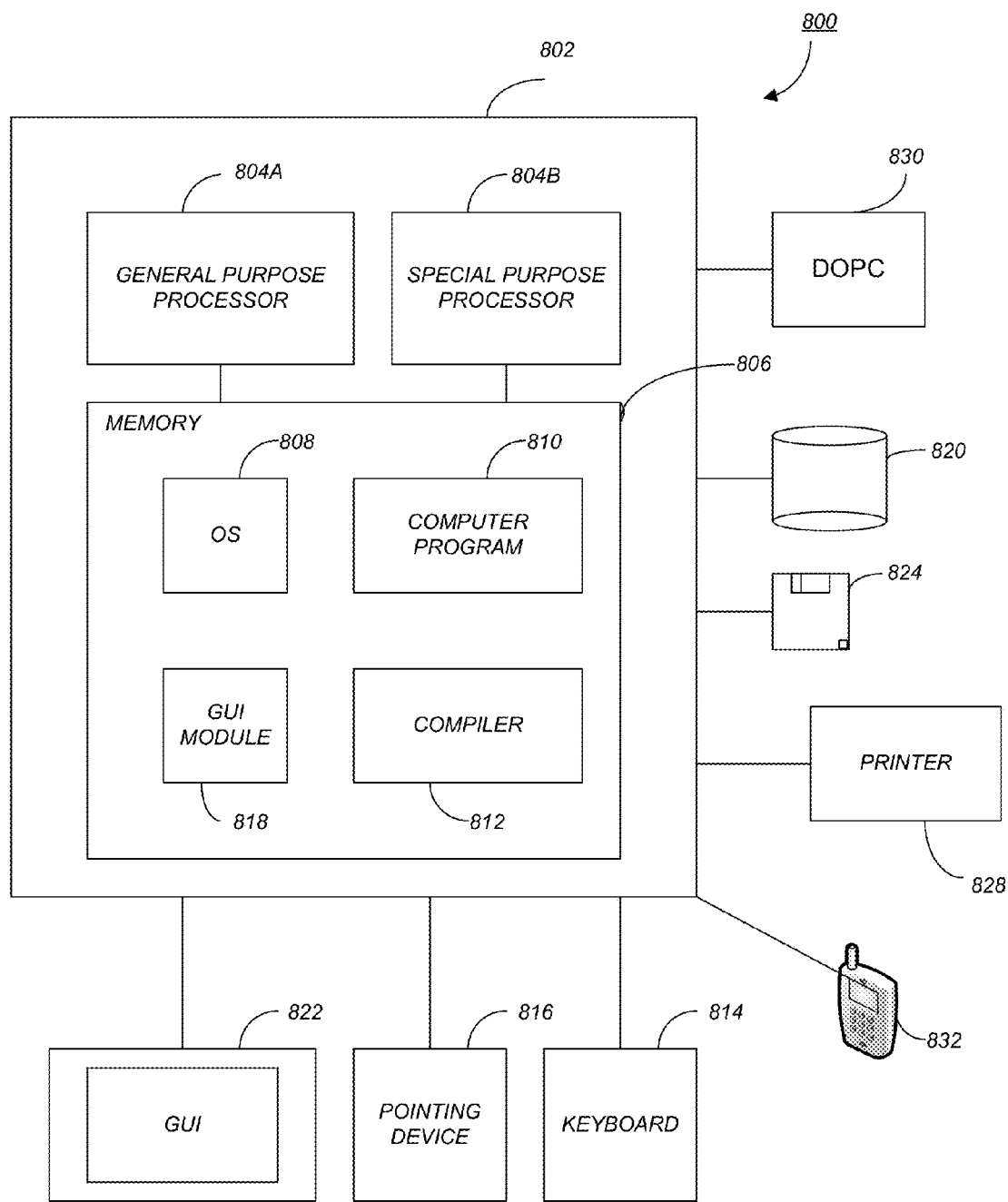
FIG. 8 is an exemplary hardware and software environment that can be used to implement one or more embodiments of the processing, control, encryption, transmitting, or receiving functions of the present invention.

FIG. 8 is an exemplary hardware and software environment 800 used to implement one or more embodiments of the processing, control, encryption, transmitting, or receiving functions of the invention. The hardware and software environment includes a computer 802 and may include peripherals. Computer 802 may be a user/client computer, server computer, or may be a database computer. The computer 802 comprises a general purpose hardware processor 804A and/or a special purpose hardware processor 804B (hereinafter alternatively collectively referred to as processor 804) and a memory 806, such as random access memory (RAM). The computer 802 may be coupled to, and/or integrated with, other devices, including input/output (I/O) devices such as a keyboard 814, a cursor control device 816 (e.g., a mouse, a pointing device, pen and tablet, touch screen, multi-touch device, etc.) and a printer 828. In one or more embodiments, computer 802 may be coupled to, or may comprise, a portable or media viewing/listening device 832 (e.g., an MP3 player, iPod™, Nook™, iPad™, portable digital video player, cellular device, personal digital assistant, etc.). In yet another embodiment, the computer 802 may comprise a multi-touch device, mobile phone, gaming system, internet enabled television, television set top box, or other internet enabled device executing on various platforms and operating systems.

In one embodiment, the computer 802 operates by the general purpose processor 804A performing instructions defined by the computer program 810 under control of an operating system 808. The computer program 810 and/or the operating system 808 may be stored in the memory 806 and may interface with the user and/or other devices to accept input and commands and, based on such input and commands and the instructions defined by the computer program 810 and operating system 808, to provide output and results.

Output/results may be presented on the display 822 or provided to another device for presentation or further processing or action. In one embodiment, the display 822 comprises a liquid crystal display (LCD) having a plurality of separately addressable liquid crystals. Alternatively, the display 822 may comprise a light emitting diode (LED) display having clusters of red, green and blue diodes driven together to form full-color pixels. Each liquid crystal or pixel of the display 822 changes to an opaque or translucent state to form a part of the image on the display in response to the data or information generated by the processor 804 from the application of the instructions of the computer program 810 and/or operating system 808 to the input and commands. The image may be provided through a graphical user interface (GUI) module 818. Although the GUI module 818 is depicted as a separate module, the instructions performing the GUI functions can be resident or distributed in the operating system 808, the computer program 810, or implemented with special purpose memory and processors.

In one or more embodiments, the display 822 is integrated with/into the computer 802 and comprises a multi-touch device having a touch sensing surface (e.g., track pod or touch screen) with the ability to recognize the presence of two or more points of contact with the surface. Examples of multi-touch devices include mobile devices or smartphones (e.g., iPhone™, Nexus S™, Droid™ devices, etc.), tablet computers (e.g., iPad™, HP Touchpad™), portable/handheld game/music/video player/console devices (e.g., iPod Touch™, MP3 players, Nintendo 3DS™, PlayStation Portable™, etc.), touch tables, and walls (e.g., where an image is projected through acrylic and/or glass, and the image is then backlit with LEDs).

Some or all of the operations performed by the computer 802 according to the computer program 810 instructions may be implemented in a special purpose processor 804B. In this embodiment, the some or all of the computer program 810 instructions may be implemented via firmware instructions stored in a read only memory (ROM), a programmable read only memory (PROM) or flash memory within the special purpose processor 804B or in memory 806. The special purpose processor 804B may also be hardwired through circuit design to perform some or all of the operations to implement the present invention. Further, the special purpose processor 804B may be a hybrid processor, which includes dedicated circuitry for performing a subset of functions, and other circuits for performing more general functions such as responding to computer program 810 instructions. In one embodiment, the special purpose processor 804B is an application specific integrated circuit (ASIC).

The computer 802 may also implement a compiler 812 that allows an application or computer program 810 written in a programming language such as COBOL, Pascal, C++, FORTRAN, or other language to be translated into processor 804 readable code. Alternatively, the compiler 812 may be an interpreter that executes instructions/source code directly, translates source code into an intermediate representation that is executed, or that executes stored precompiled code. Such source code may be written in a variety of programming languages such as Java™, Perl™, Basic™, etc. After completion, the application or computer program 810 accesses and manipulates data accepted from I/O devices and stored in the memory 806 of the computer 802 using the relationships and logic that were generated using the compiler 812.

The computer 802 also optionally comprises an external communication device such as a modem, satellite link, Ethernet card, or other device for accepting input from, and providing output to, other computers 802.

In one embodiment, instructions implementing the operating system 808, the computer program 810, and the compiler 812 are tangibly embodied in a non-transient computer-readable medium, e.g., data storage device 820, which could include one or more fixed or removable data storage devices, such as a zip drive, floppy disc drive 824, hard drive, CD-ROM drive, tape drive, etc. Further, the operating system 808 and the computer program 810 are comprised of computer program 810 instructions which, when accessed, read and executed by the computer 802, cause the computer 802 to perform the steps necessary to implement and/or use the present invention or to load the program of instructions into a memory 806, thus creating a special purpose data structure causing the computer 802 to operate as a specially programmed computer executing the method steps described herein. Computer program 810 and/or operating instructions may also be tangibly embodied in memory 806 and/or DOPC 830, thereby making a computer program product or article of manufacture according to the invention. As such, the terms "article of manufacture," "program storage device," and "computer program product," as used herein, are intended to encompass a computer program accessible from any computer readable device or media.

Of course, those skilled in the art will recognize that any combination of the above components, or any number of different components, peripherals, and other devices, may be used with the computer 802.

The processors 804a or 804b may execute a decoding program 810 using the variance structure defined by the UST, to decode the transmitted EM radiation received in the DOPC 830. Processors 804a or 804b may perform the processing functions of Blocks 608, Blocks 700-706 and/or 708-712. For example, the processors 804a or 804b may solve the eigenvector equation comprising the Rayleigh Quotient and find the vector that is a principal eigenvector of the Rayleigh Quotient, or any other algorithms described in this specification, using program 810. Computer 802 can be used as the computer(s) 506, 512, 514 in FIG. 5.

Figure 9:
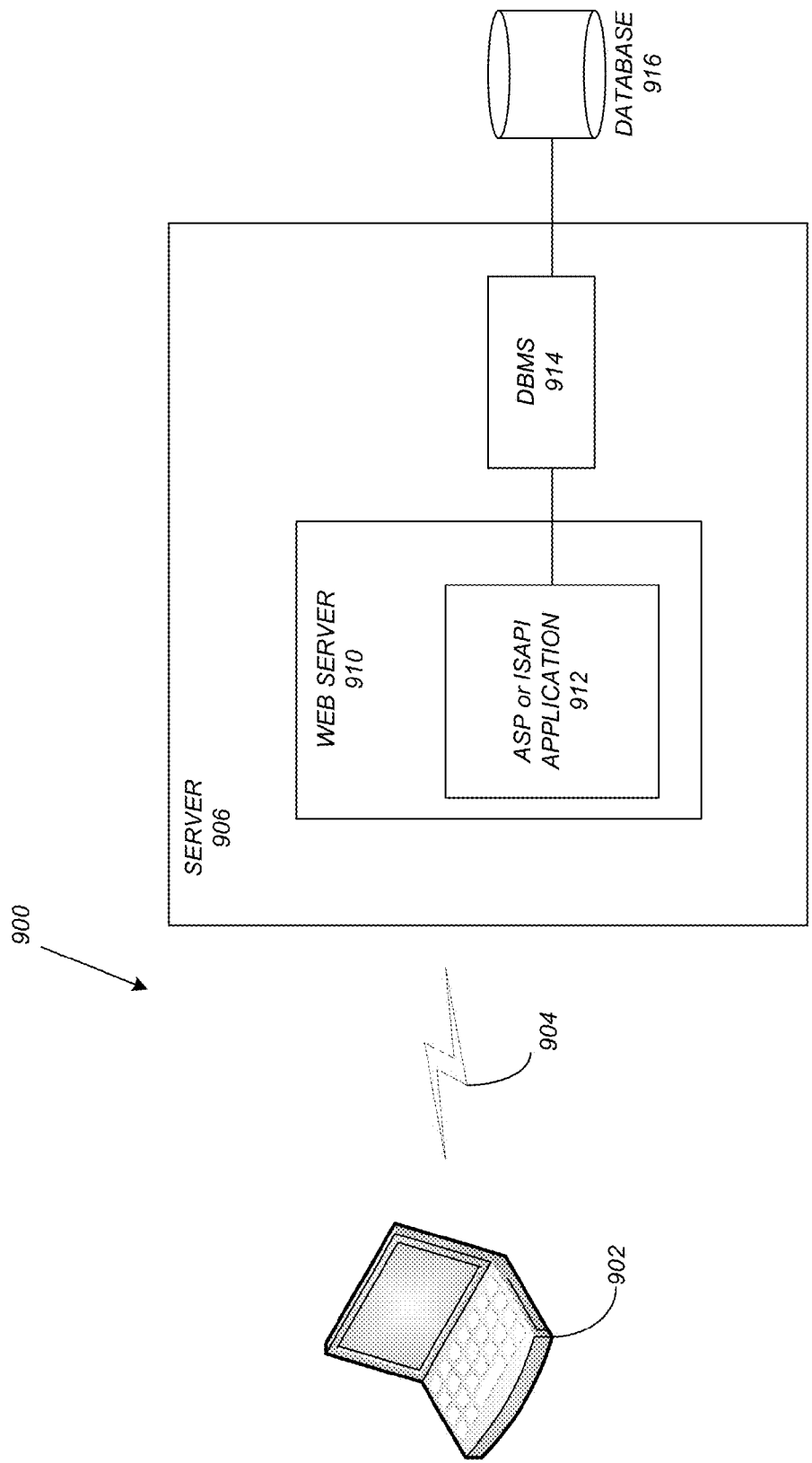
FIG. 9 schematically illustrates a typical distributed computer system using a network to connect client computers to server computers that can be used to implement one or more embodiments of the processing, control, encryption, transmitting, or receiving functions of the present invention.

FIG. 9 schematically illustrates a typical distributed computer system 900 using a network 904 to connect client computers 902 to server computers 906. A typical combination of resources may include a network 904 comprising the Internet, LANs (local area networks), WANs (wide area networks), SNA (systems network architecture) networks, or the like, clients 902 that are personal computers or workstations (as set forth in FIG. 8), and servers 906 that are personal computers, workstations, minicomputers, or mainframes (as set forth in FIG. 8). However, it may be noted that different networks such as a cellular network (e.g., GSM [global system for mobile communications] or otherwise), a satellite based network, or any other type of network may be used to connect clients 902 and servers 906 in accordance with embodiments of the invention.

A network 904 such as the Internet connects clients 902 to server computers 906. Network 904 may utilize ethernet, coaxial cable, wireless communications, radio frequency (RF), etc. to connect and provide the communication between clients 902 and servers 906. Clients 902 may execute a client application or web browser and communicate with server computers 906 executing web servers 910. Such a web browser is typically a program such as MICROSOFT INTERNET EXPLORER™, MOZILLA FIREFOX™, OPERA™, APPLE SAFARI™, etc. Further, the software executing on clients 902 may be downloaded from server computer 906 to client computers 902 and installed as a plug-in or ACTIVEX™ control of a web browser. Accordingly, clients 902 may utilize ACTIVEX™ components/component object model (COM) or distributed COM (DCOM) components to provide a user interface on a display of client 902. The web server 910 is typically a program such as MICROSOFT'S INTERNET INFORMATION SERVER™.

Web server 910 may host an Active Server Page (ASP) or Internet Server Application Programming Interface (ISAPI) application 912, which may be executing scripts. The scripts invoke objects that execute business logic (referred to as business objects). The business objects then manipulate data in database 916 through a database management system (DBMS) 914. Alternatively, database 916 may be part of, or connected directly to, client 902 instead of communicating/obtaining the information from database 916 across network 904. When a developer encapsulates the business functionality into objects, the system may be referred to as a component object model (COM) system. Accordingly, the scripts executing on web server 910 (and/or application 912) invoke COM objects that implement the business logic. Further, server 906 may utilize MICROSOFT'S™ Transaction Server (MTS) to access required data stored in database 916 via an interface such as ADO (Active Data Objects), OLE DB (Object Linking and Embedding DataBase), or ODBC (Open DataBase Connectivity).

Generally, these components 900-916 all comprise logic and/or data that is embodied in/or retrievable from device, medium, signal, or carrier, e.g., a data storage device, a data communications device, a remote computer or device coupled to the computer via a network or via another data communications device, etc. Moreover, this logic and/or data, when read, executed, and/or interpreted, results in the steps necessary to implement and/or use the present invention being performed.

Although the terms "user computer", "client computer", and/or "server computer" are referred to herein, it is understood that such computers 902 and 906 may be interchangeable and may further include thin client devices with limited or full processing capabilities, portable devices such as cell phones, notebook computers, pocket computers, multi-touch devices, and/or any other devices with suitable processing, communication, and input/output capability.

Of course, those skilled in the art will recognize that any combination of the above components, or any number of different components, peripherals, and other devices, may be used with computers 902 and 906.

The algorithms of FIG. 7a-7b, processing in FIG. 6, and/or processing in computers 506, 512, 514 can be performed in whole or in part on one or more computers (e.g., in a client server relationship as illustrated in FIG. 9).

10. Software Embodiment Overview

Embodiments of the invention are implemented as a software application on a client 902 or server computer 906. Further, as described above, the client 902 or server computer 906 may comprise a thin client device or a portable device that has a multi-touch-based display.

Thus FIGS. 7-9 illustrate a computer readable storage medium 820 encoded with computer program instructions which when accessed by a computer cause the computer to load the program instructions 810 to a memory therein 806 creating a special purpose data structure causing the computer 802 to operate as a specially programmed computer, executing a method of decoding transmitted EM radiation, comprising (a) receiving, in the specially programmed computer, the transmitted EM radiation comprising a portion of encoded EM radiation transmitted through and exiting the scattering medium and exiting the scattering medium, wherein a target inside the scattering medium encodes EM radiation transmitted to the target with a variance structure to form the encoded EM radiation; (b) decoding the transmitted EM radiation, comprising EM fields, in the computer, comprising selecting one or more of the EM fields having the variance structure; and (c) outputting the EM fields having the variance structure, wherein the outputted EM fields are time reversed to generate time reversed EM radiation irradiating the scattering medium thereby forming a focus of the time reversed EM radiation in the scattering medium with increased resolution.

REFERENCES

The following references are incorporated by reference herein.

[1] Mosk, A. P., Lagendijk, A., Lerosey, G. & Fink, M. Controlling waves in space and time for imaging and focusing in complex media. *Nat Photonics* 6, 283-292, doi: Doi10.1038/Nphoton.2012.88 (2012).

[2] Freund, I. Looking through Walls and around Corners. *Physica A* 168, 49-65 (1990).

[3] Vellekoop, I. M., Lagendijk, A. & Mosk, A. P. Exploiting disorder for perfect focusing. *Nat Photon* 4, 320-322 (2010).

[4] Vellekoop, I. M. & Mosk, A. P. Focusing coherent light through opaque strongly scattering media. *Optics Letters* 32, 2309-2311, doi:10.1364/ol.32.002309 (2007).

[5] Katz, O., Small, E. & Silberberg, Y. Looking around corners and through thin turbid layers in real time with scattered incoherent light. *Nat Photonics* 6, 549-553, doi: Doi10.1038/Nphoton.2012.150 (2012).

[6] Katz, O., Small, E., Bromberg, Y. & Silberberg, Y. Focusing and compression of ultrashort pulses through scattering media. *Nat Photonics* 5, 372-377, doi:Doi 10.1038/Nphoton.2011.72 (2011).

[7] van Putten, E. G. et al. Scattering Lens Resolves Sub-100 nm Structures with Visible Light. *Physical Review Letters* 106, 193905 (2011).

[8] Aulbach, J., Gjonaj, B., Johnson, P. M., Mosk, A. P. & Lagendijk, A. Control of LightTransmission through Opaque Scattering Media in Space and Time. *Physical Review Letters* 106, doi:Artn 103901 Doi 10.1103/Physrevlett.106.103901 (2011).

[9] Lerosey, G., De Rosny, J., Tourin, A. & Fink, M. Focusing beyond the diffraction limit with farfield time reversal. *Science* 315, 1120-1122, doi:Doi 10.1126/science.1134824 (2007).

[10] Yaqoob, Z., Psaltis, D., Feld, M. S. & Yang, C. H. Optical phase conjugation for turbidity suppression in biological samples. *Nat Photonics* 2, 110-115, doi:10.1038/nphoton.2007.297 (2008).

[11] Popoff, S., Lerosey, G., Fink, M., Boccara, A. C. & Gigan, S. Image transmission through an opaque material. *Nat Commun* 1, 81, doi:10.1038/ncomms1078 (2010).

[12] Popoff, S. M. et al. Measuring the transmission matrix in optics: an approach to the study and control of light propagation in disordered media. *Phys Rev Lett* 104, 100601 (2010).

[13] Cizmar, T. & Dholakia, K. Exploiting multimode waveguides for pure fibre-based imaging. *Nat Commun* 3, 1027, doi:10.1038/ncomms2024 (2012).

[14] Hsieh, C. L., Pu, Y., Grange, R. & Psaltis, D. Digital phase conjugation of second harmonic radiation emitted by nanoparticles in turbid media. *Optics Express* 18, 12283-12290 (2010).

[15] Vellekoop, I. M., Cui, M. & Yang, C. H. Digital optical phase conjugation of fluorescence in turbid tissue. *Applied Physics Letters* 101, doi:Artn 081108 Doi 10.1063/1.4745775 (2012).

[16] Xu, X., Liu, H. & Wang, L. V. Time-reversed ultrasonically encoded optical focusing into scattering media. *Nat Photonics* 5, 154-157 (2011).

[17] Lai, P., Xu, X., Liu, H., Suzuki, Y. & Wang, L. V. Reflection-mode time-reversed ultrasonically encoded optical focusing into turbid media. *Journal of biomedical optics* 16, 080505, doi:10.1117/1.3609001 (2011).

[18] Liu, H., Xu, X., Lai, P. & Wang, L. V. Time-reversed ultrasonically encoded optical focusing into tissue-mimicking media with thickness up to 70 mean free paths. *Journal of biomedical optics* 16, 086009, doi:10.1117/1.3609004 (2011).

[19] Wang, Y. M., Judkewitz, B., DiMarzio, C. A. & Yang, C. H. Deep-tissue focal fluorescence imaging with digitally time-reversed ultrasound-encoded light. *Nature Communications* 3, doi:Artn 928 Doi 10.1038/Ncomms1925 (2012).

[20] Si, K., Fiolka, R. & Cui, M. Fluorescence imaging beyond the ballistic regime by ultrasoundpulse-guided digital phase conjugation. *Nat Photon* 6, 657-661 (2012).

[21] Conkey, D. B., Caravaca-Aguirre, A. M. & Piestun, R. High-speed scattering medium characterization with application to focusing light through turbid media. *Optics Express* 20, 1733-1740 (2012).

[22] Redding, B., Choma, M. A. & Cao, H. Speckle-free laser imaging using random laser illumination. *Nat Photonics* 6, 355-359, doi:Doi 10.1038/Nphoton.2012.90 (2012).

[23] Yamaguchi, I. & Zhang, T. Phase-shifting digital holography. *Opt. Lett.* 22, 1268-1270 (1997).

[24] Supplementary Information DOI:10:1038/NPHOTON.2013.31, Nature Photonics, providing further information on one or more embodiments of the invention.

[25] Benjamin Judkewitz, Ying Min Wang, Roarke Horstmeyer, Alexandre Mathy, and Changhuei Yang; Speckle-scale focusing in the diffusive regime with time-reversal of variance-encoded light (TROVE); Nature Photonics 7 (4): 300-305 (2013) PMID: 23814605 [PubMed] PMCID: PMC3692396, providing further information on one or more embodiments of the present invention.

[26] U.S. Utility patent application Ser. No. 13/851,901, filed on Mar. 27, 2013, by Ying Min Wang, Benjamin Judkewitz, Charles A. DiMarzio, and Changhuei Yang, entitled "DEEP TISSUE FLUORESCENCE IMAGING USING DIGITALLY TIME-REVERSED ULTRASOUND-ENCODED LIGHT", which application claims the benefit under 35 U.S.C. Section 119(e) of U.S. Provisional Patent Application Ser. No. 61/616,347, filed on Mar. 27, 2012, by Ying Min Wang, Benjamin Judkewitz, Charles A. DiMarzio, and Changhuei Yang, entitled "DEEP TISSUE FLUORESCENCE IMAGING USING DIGITALLY TIME-REVERSED ULTRASOUND-ENCODED LIGHT", which application is incorporated by reference herein.

[27] Phys. Rev. Lett. 64 2787-2790 (1990).

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A method of irradiating a scattering medium, comprising:
    transmitting electromagnetic (EM) radiation from an EM radiation source to a target inside the scattering medium, wherein the target encodes the EM radiation with a variance structure to form encoded EM radiation;
    measuring, in a detector, transmitted EM radiation comprising at least a portion of the encoded EM radiation transmitted through and exiting the scattering medium;
    decoding the transmitted EM radiation, comprising transmitted EM fields, in a computer, comprising selecting one or more of the transmitted EM fields having the variance structure; and
    irradiating the scattering medium with time reversed EM radiation from a spatial light modulator (SLM), the time reversed EM radiation generated from time reversing the one or more transmitted EM fields having the variance structure, thereby forming a focus of the time reversed EM radiation in the scattering medium.

2. The method of claim 1, wherein the decoding further comprises calculating one or more variances or characteristics of variances of the transmitted EM radiation.

3. The method of claim 1, further comprising:
    detecting, on a detector, output radiation based on an interaction between the time reversed EM radiation and the scattering medium, to produce a detected signal; and
    subtracting a background from the detected signal, in a computer, to obtain an output that at least approximates an interaction between a complete time reversed field, of all of the encoded EM radiation, and the target.

4. The method of claim 1, wherein the EM radiation forms speckle at the target and the variance structure is such that a size of the focus is at most limited by the speckle.

5. The method of claim 1, wherein the variance structure is such that a spatial extent of the focus is at most 10 micrometers.

6. The method of claim 1, wherein the detector and the SLM are in a Digital Optical Phase Conjugation (DOPC) device and the scattering medium includes at least a portion that does not transmit a ballistic component of the EM radiation or wherein the scattering medium scatters the EM radiation in a diffusive regime.

7. The method of claim 1, wherein the forming forms the focus with increased resolution.

8. The method of claim 1, further comprising:
    forming the EM radiation comprising a plurality of EM fields;
    transmitting signals from a signal generator to form the target comprising a plurality of spatially shifted and spatially overlapping signals, wherein each of the EM fields is encoded by each of the spatially shifted and spatially overlapping signals, to form the encoded EM radiation comprising a plurality of encoded EM fields and the transmitted EM radiation comprising the transmitted EM fields;
    for each one of the spatially shifted and spatially overlapping signals, forming a matrix representing the transmitted EM fields encoded by the one of the spatially shifted and spatially overlapping signals, thereby forming a plurality of matrices;

calculating a sum of the matrices and one or more differences of one or more pairs of the matrices;

the decoding comprising finding a field vector v having higher variance for the sum and a smaller variance for the one or more differences; and finding a complex conjugate of the field vector v;

wherein the time reversed EM radiation comprises time reversed fields generated from the complex conjugate.

9. The method of claim 8, wherein the field vector v represents a mode of zero variance in the differences.

10. The method of claim 8, wherein the forming of the EM radiation comprises randomizing the EM radiation to form the plurality of the EM fields comprising random EM fields.

11. The method of claim 8, further comprising digitally scanning the focus of the time reversed EM radiation by weighing the transmitted EM fields in the matrices with prefactors that virtually and spatially move an intersection point of the signals.

12. The method of claim 8, wherein the decoding comprises maximizing a Rayleigh Quotient of the matrices.

13. The method of claim 8, wherein the signals are ultrasound foci that encode the EM fields to form the transmitted EM fields comprising frequency shifted EM fields.

14. The method of claim 12, wherein the decoding comprises solving an eigenvector equation comprising the Rayleigh Quotient and wherein the field vector v is a principal eigenvector of the Rayleigh Quotient.

15. The method of claim 14, further comprising forming four of the spatially shifted and overlapping signals and four of the matrices $C_1$, $C_2$, $C_3$, and $C_4$.

16. The method of claim 15, wherein $$v = C_{1+2+3+4}^{*0.5}(C_{1-4}C_{1-4}^{*}+C_{2-3}C_{2-3}^{*})^{-0.5} \cdot$$
$$eig[(C_{1-4}C_{1-4}^{*}+C_{2-3}C_{2-3}^{*})^{-0.5} \cdot (C_{1+2+3+4} C_{1+2+3+4}^{*})(C_{1-4}C_{1-4}^{*}+C_{2-3}C_{2-3}^{*-0.5}].$$

17. The method of claim 13, further comprising shaping the ultrasound foci to produce the variance structure.

18. The method of claim 13, wherein:

each of the EM fields produce different realizations r of the frequency-shifted EM fields, each realization r is represented as a row of the matrices, and each row comprises one of the transmitted EM fields measured for one of the realizations.

19. The method of claim 17, further comprising measuring the transmitted EM fields comprising the frequency-shifted EM fields via digital phase-shifting holography.

20. An apparatus for irradiating a target in a scattering medium, comprising:

an ultrasound transducer for transmitting ultrasound that forms a target inside a scattering medium;

a coherent electromagnetic (EM) radiation source for transmitting EM radiation to the target inside the scattering medium, wherein the target encodes the EM radiation with a variance structure to form encoded EM radiation; and a digital optical phase conjugation device (DOPC) positioned to measure transmitted EM radiation comprising at least a portion of the encoded EM radiation transmitted through and exiting the scattering medium, the DOPC comprising:

a detector to receive the transmitted EM radiation comprising transmitted EM fields;

a computer configured to decode the transmitted EM radiation, wherein the computer selects one or more of the transmitted EM fields having the variance structure; and a spatial light modulator (SLM) for irradiating the scattering medium with time reversed EM radiation generated from time reversing the one or more transmitted EM fields having the variance structure, thereby forming a focus of the time reversed EM radiation in the scattering medium.

21. The apparatus of claim 20, wherein the focus is formed with increased resolution.

22. A non-transitory computer readable storage medium encoded with computer program instructions which when accessed by a computer cause the computer to load the program instructions to a memory therein creating a special purpose data structure causing the computer to operate as a specially programmed computer, executing a method of decoding transmitted electromagnetic (EM) radiation, comprising:

(a) receiving, in the specially programmed computer, transmitted EM fields of the transmitted EM radiation, the transmitted EM radiation comprising a portion of encoded EM radiation transmitted through and exiting a scattering medium, wherein a target inside the scattering medium encodes EM radiation transmitted to the target with a variance structure to form the encoded EM radiation;

(b) selecting, in the specially programmed computer, one or more of the transmitted EM fields having the variance structure;

(c) outputting, from the specially programmed computer, the transmitted EM fields having the variance structure, wherein the outputted transmitted EM fields are time reversed to generate time reversed EM radiation irradiating the scattering medium thereby forming a focus of the time reversed EM radiation in the scattering medium.

23. The non-transitory computer readable storage medium of claim 22, wherein:

the target comprises a plurality of signals, the signals are spatially shifted with respect to each other and spatially overlap with each other, the EM radiation comprises EM fields and each of the EM fields are encoded by each of the signals to form the encoded EM radiation, the method of decoding the transmitted EM radiation further comprises, in the computer:

for each one of the signals, obtaining a matrix representing the transmitted EM fields encoded by the one of the signals, thereby obtaining a plurality of matrices, calculating a sum of the matrices and one or more differences of one or more pairs of the matrices, finding a field vector v having higher variance for the sum and a smaller variance for the one or more differences, and the time reversed EM radiation comprises time reversed fields generated from the complex conjugate of the field vector v.

24. The non-transitory computer readable storage medium of claim 22, wherein the focus is formed with increased resolution.

25. The apparatus of claim 20, wherein:

the target comprises a plurality of ultrasound signals, the ultrasound signals are spatially shifted with respect to each other and spatially overlap with each other, the EM radiation comprises EM fields and each of the EM fields are encoded by each of the ultrasound signals to form the encoded EM radiation, for each one of the ultrasound signals, the computer obtains a matrix representing the transmitted EM fields encoded by the one of the ultrasound signals, thereby obtaining a plurality of matrices, the computer calculates a sum of the matrices and one or more differences of one or more pairs of the matrices, the decoding comprises finding a field vector v having higher variance for the sum and a smaller variance for the one or more differences, and the time reversed EM radiation comprises time reversed fields generated from a complex conjugate of the field vector v.

* * * * *